United States Patent
Schnorrenberg et al.

(10) Patent No.: US 6,413,959 B1
(45) Date of Patent: Jul. 2, 2002

(54) METHOD OF TREATING DEPRESSION WITH ARYLGLYCINAMIDE DERIVATIVES

(75) Inventors: Gerd Schnorrenberg, Gau-Algesheim; Horst Dollinger; Franz Esser, both of Ingelheim am Rhein; Hans Briem, Budenheim; Birgit Jung, Bingen; Georg Speck, Ingelheim am Rhein, all of (DE)

(73) Assignee: Boehringer Ingelheim KG, Ingelheim am Rhein (DE)

( * ) Notice: Subject to any disclaimer, the term of this patent is extended or adjusted under 35 U.S.C. 154(b) by 0 days.

(21) Appl. No.: 09/971,358

(22) Filed: Oct. 5, 2001

Related U.S. Application Data

(62) Division of application No. 09/752,730, filed on Jan. 3, 2001, now Pat. No. 6,303,601, which is a division of application No. 09/507,581, filed on Feb. 18, 2000, now Pat. No. 6,251,909, which is a division of application No. 08/930,704, filed as application No. PCT/EP96/01548 on Apr. 11, 1996, now Pat. No. 6,124,296.

(30) Foreign Application Priority Data

Apr. 14, 1995 (DE) .......................... 195 14 112
May 25, 1995 (DE) .......................... 195 19 245

(51) Int. Cl.$^7$ ............................ A61P 25/24
(52) U.S. Cl. ............... 514/235.5; 514/252.1; 514/254.11; 514/255.04; 514/278; 514/316; 514/318; 514/322; 514/326; 514/329; 514/330; 514/331
(58) Field of Search .......... 514/235.5, 252.1, 514/255.04

(56) References Cited

U.S. PATENT DOCUMENTS

| | | | |
|---|---|---|---|
| 3,518,274 A | 6/1970 | Strycker | |
| 3,862,946 A | 1/1975 | Havera | |
| 3,906,100 A | 9/1975 | Havera | |
| 5,710,155 A | 1/1998 | Schnorrenberg et al. | |
| 5,861,509 A | 1/1999 | Schnorrenberg et al. | |
| 6,103,719 A | 8/2000 | Esser et al. | |
| 6,121,262 A | 9/2000 | Schnorrenberg et al. | |
| 6,124,296 A | 9/2000 | Schnorrenberg et al. | |
| 6,251,909 B1 | 6/2001 | Schnorrenberg et al. | |
| 6,294,556 B1 | 9/2001 | Schnorrenberg et al. | |
| 6,303,601 B2 | 10/2001 | Schnorrenberg et al. | |

FOREIGN PATENT DOCUMENTS

| | | |
|---|---|---|
| WO | WO 94/01402 | 1/1994 |
| WO | WO 94/10146 | 5/1994 |
| WO | WO 5/26335 | 10/1995 |
| WO | WO 96/08480 | 3/1996 |

OTHER PUBLICATIONS

Nagarajan, K., et al., "A Novel Displacement Reaction On α–Chlorodiphenylacetamides," *Tetrahedron Letts.* 15:1387–1390, Pergamon Press Ltd. (1967).
Patel, B.M., et al., "Evaluation of New Series of Lignocaine Analogues," *Indian J. Pharm.* 33:86–89, Indian Pharmaceutical Association (1971).
Patel, B.M., et al., "Evaluation of new series of lignocaine analogs," *Chem. Abstr.* 76:7, Abstract No. 54228t, Chemical Abstracts Service (1972).
Shah, K.J., and Trivedi, J.J., "Potential Local Anaesthetics. Part V. Synthesis of Basic N–(Substituted benzyl) Phenyl Acetamides," *Indian J. Appl. Chem.* 30:11–13, Indian Chemical Society (1967).
Shah, K.J., and Trivedi, J.J., "Potential Local Anesthetics. V. Synthesis of Basic N–(substituted benzyl)phenylacetamides," *Chem. Abstr.* 68:5715, Abstract No. 59230g, Chemical Abstracts Service (1968).
International Search Report for International Application No. PCT/EP96/01548, mailed Aug. 20, 1996.

*Primary Examiner*—Robert W. Ramsuer
(74) *Attorney, Agent, or Firm*—Sterne, Kessler, Goldstein & Fox, P.L.L.C.

(57) ABSTRACT

The invention relates to new arylglycinamide derivatives of general formula I

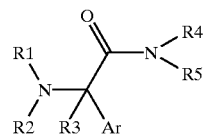

and the pharmaceutically acceptable salts thereof, wherein $R^1$ and $R^2$ together with the N to which they are bound form a ring of the formula

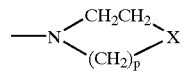

wherein
p is 2 or 3 and
X denotes oxygen, $N(CH_2)_n R^6$ or $CR^7 R^8$,
and $R^3$, $R^4$, $R^5$, $R^6$, $R^7$, $R^8$, Ar and n have the meanings given in the specification, and the preparation and use thereof. The new compounds are valuable neurokinin (tachykinin)-antagonists.

85 Claims, No Drawings

METHOD OF TREATING DEPRESSION WITH ARYLGLYCINAMIDE DERIVATIVES

CROSS REFERENCE TO RELATED APPLICATIONS

This application is a division of application Ser. No. 09/752,730, filed Jan. 3, 2001, now U.S. Pat. No. 6,303,601, which is a division of application Ser. No. 09/507,581, filed Feb. 18, 2000, now U.S. Pat. No. 6,251,909, which is a division of application Ser. No. 08/930,704, §102(e) date Oct. 29, 1997, now U.S. Pat. No. 6,124,296, which is the National Stage of International Application No. PCT/EP96/01548, filed Apr. 11, 1996.

SUMMARY OF THE INVENTION

The invention relates to new arylglycinamide derivatives of general formula I

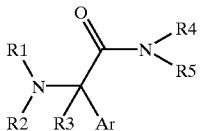

I and the pharmaceutically acceptable salts thereof, processes for preparing them and pharmaceutical compositions containing these compounds. The compounds are valuable neurokinin (tachykinin) antagonists.

DETAILED DESCRIPTION OF THE INVENTION

The abbreviations used in the specification and claims are explained as follows:

CDI=Carbonyldiimidazole
DCCI=Dicyclohexylcarbodiimide
HOBt=1-Hydroxybenzotriazole
THF=Tetrahydrofuran
DMF=Dimethylformamide
RT=Room temperature
DMAP=4-Dimethylaminopyridine
TBTU=O-Benzotriazolyl-tetramethyluroniumtetrafluoroborate In order to show the formulae, a simplified representation is used. In the representation of the compounds all $CH_3$-substituents are represented by a single bond, and for example the following formula

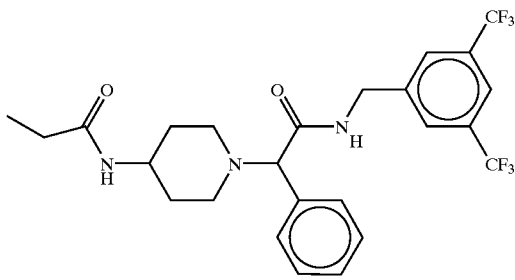

represents

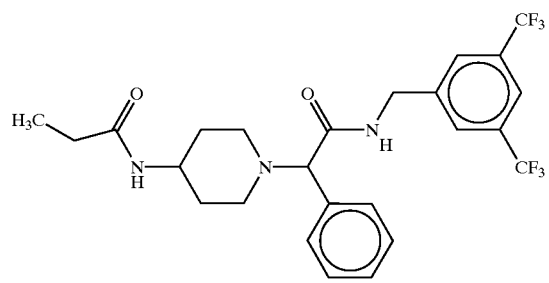

The invention relates to new aryiglycinamide derivatives of general formula I

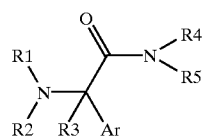

I or the pharmaceutically acceptable salts thereof,
wherein
Ar denotes unsubstituted or mono- to pentasubstituted phenyl, or unsubstituted or mono- or di-substituted naphthyl, [in which the substituents of the phenyl and naphthyl independently of each other denote halogen (F, Cl, Br, I), OH, $(C_{1-4})$alkyl, O—$(C_{1-4})$alkyl, $CF_3$, $OCF_3$ or $NR^9R^{10}$ (wherein $R^9$ and $R^{10}$ independently of each other denote H, methyl or acetyl)] or Ar is phenyl'substituted by —$OCH_2O$— or —$O(CH_2)_2O$—;
$R^1$ and $R^2$ together with the N to which they are bound form a ring of the formula

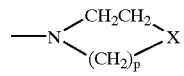

wherein
p is 2 or 3,
X denotes oxygen, $N(CH_2)_nR^6$ or $CR^7R^8$, wherein
n is 0, 1 or 2,
$R^6$ is $(C_{3-7})$cycloalkyl, phenyl or naphthyl, wherein the phenyl may be mono- to tri-substituted by halogen (F, Cl, Br, I), $(C_{1-4})$alkyl, O—$(C_{1-4})$alkyl, $CF_3$, $OCF_2$ or $NR^{15}R^{16}$ (wherein $R^{15}$ and $R^{16}$ independently of each other denote H, methyl or acetyl);
$R^7$ and $R^8$ have one of the following meanings:
  a) $R^7$ and $R^8$ represent H if $R^3$ is unsubstituted or substituted phenyl,
  b) $R^7$ is phenyl, phenyl substituted by 1 to 3 substituents [wherein the substituents independently of one another denote halogen (F, Cl, Br, I), $(C_{1-4})$alkyl, O—$(C_{1-4})$alkyl, $CF_3$ or $OCF_3$], piperidinyl, 1-methylpiperidinyl,

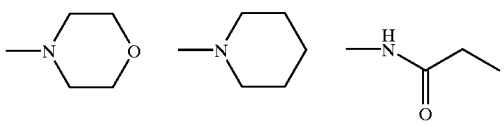

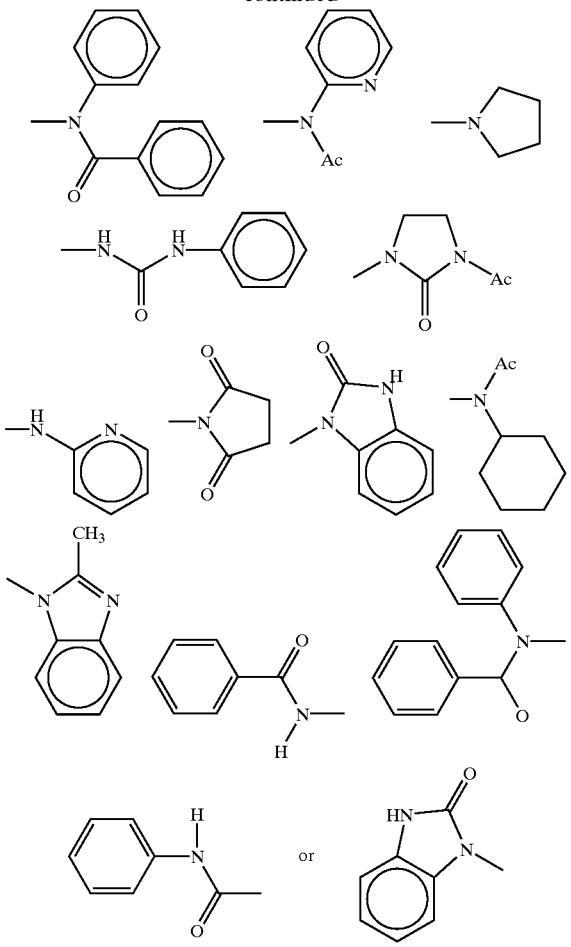

if R⁸ is H, —CONH₂, —NHC(O)CH₃, —N(CH₃)C(O)CH₃, CN

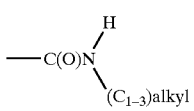

or —C(O)N((C₁₋₃)alkyl)₂ or
c) R⁷ and R⁸ together form the group

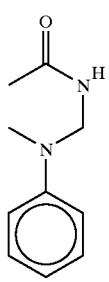

$R^3$ denotes H, $(C_{1-4})$alkyl, unsubstituted or mono- to tri-substituted phenyl, wherein the substituents independently of one another represent halogen (F, Cl, Br, I), $(C_{1-4})$alkyl, O—$(C_{1-4})$alkyl, $CF_3$, $OCF_3$ or $NR^{17}R^{18}$ (wherein $R^{17}$ and $R^{18}$ independently of one another denote H, methyl or acetyl);

$R^4$ denotes phenyl$(C_{1-4})$alkyl or naphthyl$(C_{1-4})$alkyl, wherein phenyl may be substituted by 1 to 3 substituents, wherein the substituents independently of one another are halogen (F, Cl, Br, I), $(C_{1-4})$alkyl, O—$(C_{1-4})$alkyl, $CF_3$, $OCF_3$ or $NR^{19}R^{20}$ (wherein $R^{19}$ and $R^{20}$ independently of one another denote H, methyl or acetyl); and $R^5$ denotes H, $(C_{1-4})$alkyl, $(C_{3-6})$cycloalkyl, $CH_2COOH$, —$CH_2C(O)NH_2$, —OH or phenyl$(C_{1-4})$alkyl.

The compounds according to the invention are valuable neurokinin (tachykinin) antagonists which have both substance P-antagonism and also neurokinin A- or neurokinin B-antagonistic properties. They are useful for the treatment and prevention of neurokinin-mediated diseases.

Compounds of general formula I may contain acid groups, chiefly carboxyl groups, and/or basic groups such as, for example, amino functions. Compounds of general formula I may therefore be obtained either as internal salts, as salts with pharmaceutically acceptable inorganic acids such as hydrochloric acid, sulphuric acid, phosphoric acid or sulphonic acid or organic acids (such as, for example, maleic acid, fumaric acid, citric acid, tartaric acid or acetic acid) or as salts with pharmaceutically acceptable bases such as alkali or alkaline earth metal hydroxides or carbonates, zinc or ammonium hydroxides or organic amines such as, for example, diethylamine, triethylamine or triethanolamine, etc.

The compounds according to. the invention may occur as racemates but may also be obtained as pure enantiomers, i.e. in (R)- or (S)-form. They may also occur as diastereoisomers or mixtures thereof.

The preferred compounds of general formula I are those wherein
$R^1$ and $R^2$ together with the N to which they are bound form a 6-membered ring of the formula

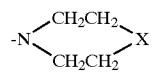

wherein

X denotes $N(CH_2)_nR^6$ or $CR^7R^8$, wherein n, $R^6$, $R^7$ and $R^8$ are defined as in claim 1.

Particular mention should be made of compounds of formula I wherein

X is $N(CH_2)_nR^6$ wherein n is 0, 1 or 2 and $R^6$ is $(C_{3-7})$cycloalkyl or phenyl, particularly those compounds wherein n is 0 and $R^6$ is $(C_{3-7})$cycloalkyl, particularly those compounds wherein $R^6$ is cyclobutyl or cyclohexyl.

Mention should also be made of compounds of formula I wherein $R^7$ and $R^8$ have one of the following meanings:
a) $R^7$ and $R^8$ denote H when $R^3$ is unsubstituted or substituted phenyl,
b) $R^7$ is phenyl, piperidinyl

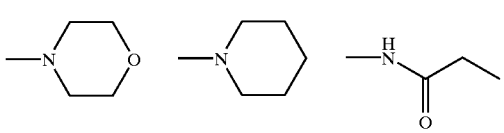

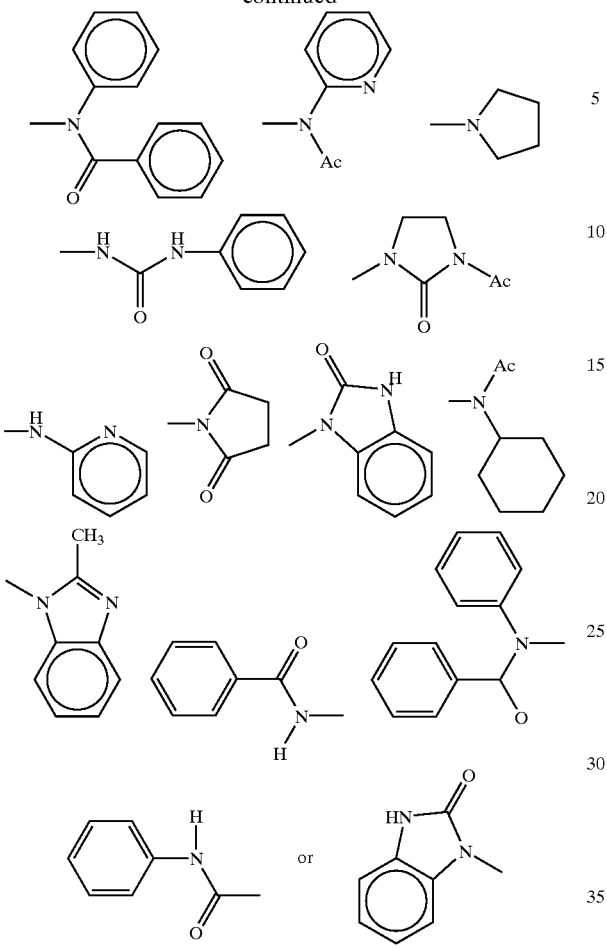

if $R^8$ is H, —CONH$_2$, —NHC(O)CH$_3$, —N(CH$_3$)C(O)CH$_3$ or CN, or c) $R^7$ and $R^8$ together form the group

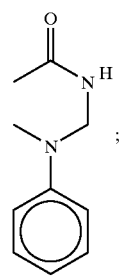

particularly those wherein
$R^7$ and $R^8$ have one of the following meanings:
a) $R^7$ and $R^8$ denote H when $R^3$ is unsubstituted or substituted phenyl,
b) $R^7$ is phenyl,

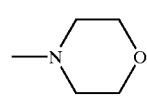 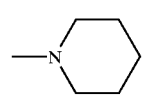 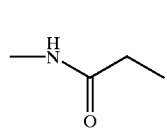

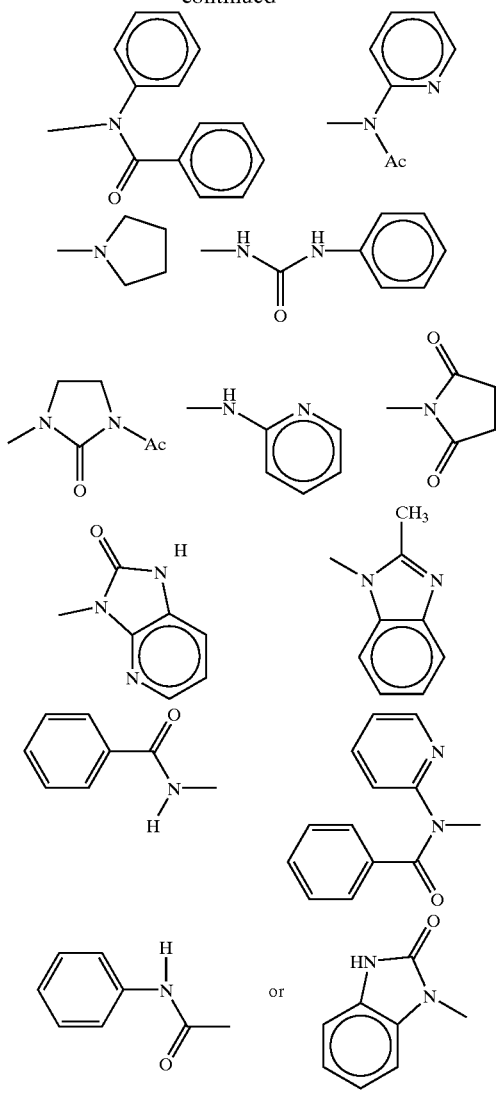

when $R^8$ is H, —CONH$_2$ or CN, or c) $R^7$ and $R^8$ together form the group

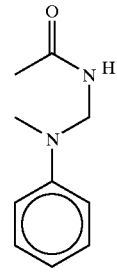

The preferred compounds are those wherein $R^7$ denotes phenyl

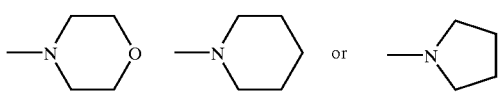 or 

and R[8] is H or CN, particularly those wherein R[7] is pyridino and R[8] is H.

Of the compounds defined above, the preferred ones are those wherein

Ar denotes unsubstituted or mono- or di-substituted phenyl, or unsubstituted naphthyl [wherein the substituents of the phenyl independently of one another are halogen (F, Cl, Br, I), OH, methyl, methoxy, $CF_3$, $OCF_3$ or dimethylamine] or Ar is phenyl substituted by —$OCH_2O$—, this group connecting positions 2 and 3 or 3 and 4 of the phenyl, particularly those wherein Ar denotes unsubstituted or mono- or di-substituted phenyl, or unsubstituted naphthyl [wherein the substituents of the phenyl independently of one another are halogen (F, Cl, Br), methoxy or $CF_3$] or Ar is phenyl substituted by —$OCH_2O$—, this group connecting positions 2 and 3 or 3 and 4 of the phenyl.

The preferred compounds are those wherein Ar is phenyl, 3,4-dichlorophenyl, 3,4-dimethoxyphenyl or 3,4-methylenedioxyphenyl.

Of the compounds defined above, particular mention should be made of those wherein $R^3$ is phenyl or preferably H.

Of the compounds defined above, mention should also be made of those wherein $R^4$ denotes phenyl($C_{1-3}$)alkyl, wherein phenyl may be substituted by 1 or 2 substituents, the substituents independently of one another being halogen (F, Cl, Br, I), methyl, methoxy, $CF_3$ or $OCF_3$; and $R^5$ denotes H, ($C_{1-3}$)alkyl, $CH_2COOH$, —$CH_2C(O)NH_2$ or phenethyl, particularly those compounds wherein $R^4$ is

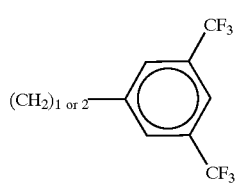

and $R^5$ denotes H or $CH_3$.

The following compounds are preferred:

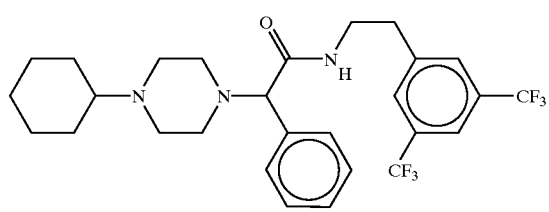

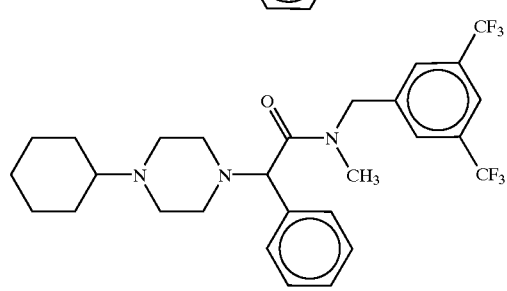

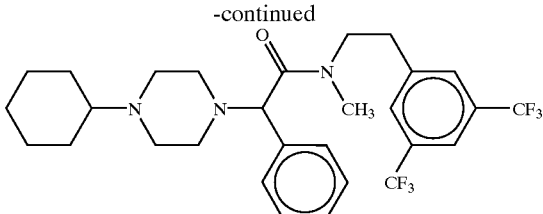

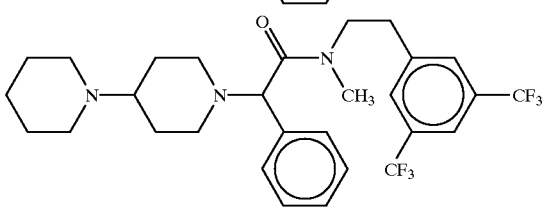

and

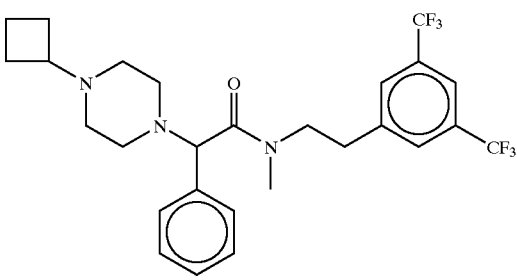

The term naphthyl used above includes both 1-naphthyl and 2-naphthyl.

Test results for compounds according to the invention:

The receptor affinity for the $NK_1$-receptor (substance P-receptor) is determined on human lymphoblastoma cells (IM-9) with cloned $NK_1$-receptors, measuring the displacement of $^{125}$I-labelled substance P. The $K_i$-values thus obtained demonstrate the efficacy of the compounds:

|  | $K_i$ |
| --- | --- |
| Compound of Example 3: | 1.4 nM |
| Compound of Example 4: | 1.0 nM |
| Compound of Example 5: | 1.3 nM |
| Compound of Example 33: | 1.3 nM |
| Compound of Example 45: | 1.6 nM |
| Compound of Example 46: | 1.4 nM |
| Compound of Example 52: | 1.1 nM |
| Compound of Example 53: | 2.3 nM |
| Compound of Example 58: | 6.4 nM |
| Compound of Example 59: | 4.2 nM |
| Compound of Example 65: | 9.2 nM |
| Compound of Example 66: | 1.4 nM |
| Compound of Example 68: | 1.5 nM |
| Compound of Example 70: | 2.8 nM |
| Compound of Example 71: | 2.1 nM |
| Compound of Example 72: | 6.8 nM |
| Compound of Example 73: | 1.7 nM |
| Compound of Example 74: | 11.8 nM |
| Compound of Example 75: | 180 nM |
| Compound of Example 76: | 7.0 nM |

The compounds according to the invention are valuable neurokinin (tachykinin) antagonists which have, in particular, $NK_1$-antagonism, but also $NK_2$- and $NK_3$-antagonistic properties.

The compounds according to the invention are valuable neurokinin (tachykinin) antagonists which have both substance P-antagonism and also neurokinin A- or neurokinin B-antagonistic properties. They are useful for the treatment and prevention of neurokinin-mediated diseases: treatment and prevention of inflammatory and allergic diseases of the respiratory tract, such as asthma, chronic bronchitis, emphysema, rhinitis or coughs, eye diseases such as conjunctivitis and iritis, skin diseases such as dermatitis in contact eczema, urticaria, psoriasis, sunburn, insect bites and stings, neurodermitis, itching and postherpetic pain, diseases of the gastrointestinal tract such as gastric and duodenal ulcers, ulcerative colitis, Crohn's disease, irritable bowel, Hirschsprung's disease;

diseases of the joints such as rheumatoid arthritis, reactive arthritis and Reiter'syndrome;

for treating diseases of the central nervous system such as dementia, Alzheimer's disease, schizophrenia, psychosis, depression, headaches (e.g. migraine or tension headaches) and epilepsy;

for the treatment of tumours, collagenosis, dysfunction of the urinary tract, haemorrhoids, nausea and vomiting, triggered for example by radiation or cytostatic therapy or motion and pain of all kinds.

The invention therefore also relates to the use of the compounds according to the invention as remedies and pharmaceutical preparations which contain these compounds. They are preferably for use in humans. The compounds according to the invention may be administered by intravenous, subcutaneous, intramuscular, intraperitoneal or intranasal route or by inhalation, by transdermal route, if desired with the aid of iontophoresis or enhancers known from the literature, and by oral route.

For parenteral administration, the compounds of formula I or the physiologically acceptable salts thereof, optionally with conventional substances such as solubilisers, emulsifiers or other adjuvants, may be made into solutions, suspensions or emulsions. Suitable solvents include, for example, water, physiological saline solutions or alcohols, e.g. ethanol, propanediol or glycerol, sugar solutions such as glucose or mannitol solutions or a mixture of various solvents.

In addition, the compounds may be administered by means of implants, e.g. of polylactide, polyglycolide or polyhydroxybutyric acid or by means of intranasal preparations.

The oral effectiveness of compounds of general formula I can be demonstrated using the following standard test:

Inhibition of the lowering of blood pressure caused by $NK_1$ in anaesthetised guinea pigs.

Guinea pigs weighing 300–500 grams were anaesthetised with pentobarbital (50 mg/kg i.p.), intubated and mechanically ventilated with 10 ml of ambient air per kg of body weight at a rate of 60 breaths per minute. The blood pressure was measured in the blood flow through the carotid artery. In order to introduce substances intravenously, the jugular vein was cannulated.

By the intravenous administration of the $NK_1$-agonist [$\beta Ala^4$, $Sar^9$, $Met(O_2)^{11}$] SP(4–11) (0.2 μmol/kg) a brief lowering of the blood pressure was triggered which was repeated at 10 minute intervals by repeatedly giving the $NK_1$-agonist.

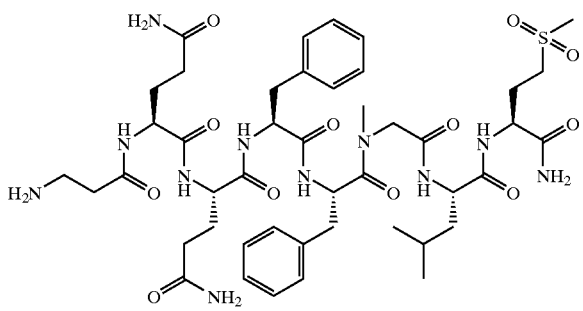

The neurokinin-antagonist was then administered by intraduodenal route and at 10 minute intervals a lowering of blood pressure was induced by means of the $NK_1$-agonist.

The inhibition of the lowering of blood pressure caused by the above-mentioned $NK_1$-agonist was measured before and after treatment with the neurokinin-antagonist.

The compound of Example 5 yielded an $ID_{50}$ of 1.4 mg/kg. ($ID_{50}$ is the dose which inhibits the lowering of blood pressure caused by the $NK_1$-agonist by 50%.)

The compounds according to the invention may be prepared by generally known methods.

The compounds may be prepared in various ways. The two commonest methods are shown in the following scheme:

Method A. The carboxylic acid may be linked to the amine $HN(R^5)R^4$ in various ways. The usual methods are coupling methods such as those used in peptide chemistry. A coupling reagent such as TBTU, DCCI/HOBt, CDI, etc., is added to the coupling partners in an approximately equivalent amount. Suitable solvents are DMF, THF, $CH_2Cl_2$, $CHCl_3$, acetonitrile or other inert solvents or mixtures thereof. The appropriate temperature range is between −50° C. and +120° C., preferably between 0° C. and 40° C.

The carboxylic acid may also initially be converted by means of $SOCl_2$, $SO_2Cl_2$, $PCl_3$, $PCl_5$ or $PBr_3$ or mixtures thereof, by known methods, into the corresponding acid halide which is subsequently reacted with the amine $HN(R^5)R^4$ in an inert solvent such as $CH_2Cl_2$, THF or dioxane at temperatures between −50° C. and +100° C., typically between 0° C. and 20° C.

Another alternative is to convert the carboxylic acid initially into the alkylester, usually the methylester, by known methods and then to react this ester with the amine $HN(R^5)R^4$ in an inert solvent such as DMF, dioxane or THF. The reaction temperatures are between 20° C. and 150° C., typically between 50° C. and 120° C. The reaction may also be carried out in a pressurised container.

Process B. In this, the α-halo-arylacetamide derivative obtained according to known procedures is reacted with the amine $R^1(R^2)NH$, thereby generating hydrogen halide. In order to mop up the cleaved (or excess) hydrogen halide, inorganic bases are used such as $K_2CO_3$, $NaHCO_3$ or $CaCO_3$, or organic bases may be used such as triethylamine, Hung base, pyridine or DMAP, or an excess of the amine $R^1(R^2)NH$ may be used. DMF, THF, dioxane or other inert solvents are used. The temperature range for the reaction is from 0 to 100° C., typically from 10 to 80° C.

Process C. The compounds according to the invention in which $R^5$ is not H may also be prepared as follows: first of all, the corresponding compound in which $R^5$ is H is synthesised according to process A or B. Then N-alkylation is carried out as follows in order to introduce alkyl, cycloalkyl or $CH_2COOH$. The compound according to the invention wherein $R^5$ is H is deprotonated with an equivalent quantity of NaH, $NaNH_2$, KOH, $NaOCH_3$ or some other strong base. Anhydrous inert solvents such as THF, dioxane or diethylether are used. Then the corresponding alkylating agent is added slowly in the form of the corresponding halide, tosylate or mesylate. The reaction is carried out in the temperature range from −50° C. to +100° C., typically between 0° C. and +50° C. The method is described in detail in Example 33.

EXAMPLE 1

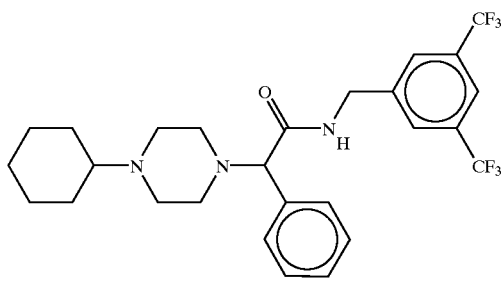

1st Step: 2.2 g of 1-cyclohexylpiperazine were dissolved in 150 ml of anhydrous DMF, mixed with 2 g of $K_2CO_3$, stirred at room temperature for 20 minutes and then cooled to 5° C. 2.7 g of methyl (R,S)-α-bromophenylacetic acid were added and the suspension was stirred overnight at RT. The precipitate was filtered off and the filtrate was evaporated down. The residue was taken up in ethyl acetate, extracted twice with 10%. $KHCO_3$ solution and once with saturated NaCl solution. The organic phase was dried over $Na_2SO_4$, filtered and evaporated down, and 3.7 g of (R,S)-1-cyclohexyl-4-(methyl 2-phenylacetate)piperazine were obtained in the form of a yellow oil. Yield: about 100%.

2nd Step: 2.3 g of the product of the first step were dissolved in 10 ml of methanol, mixed with 14 ml of 1N NaOH and the resulting emulsion was stirred overnight at room temperature. The clear reaction solution was neutralised by the addition of 14 ml of 1N HCl, evaporated to dryness, the residue was treated with isopropanol and the solid matter was collected by suction filtration. The filtrate was evaporated down and the residue was triturated again with isopropanol, the solid matter was suction filtered and combined with the solid obtained earlier. In this way, 1.6 g of (R,S)-1-cyclohexyl-4-(2-phenylacetic acid) -piperazine were obtained as a white solid.

Yield: 75%.

3rd Step: 0.6 g of the product of the second step, 0.48 g of 3,5-bis-(trifluoromethyl)-benzylamine and 0.32 g of HOBT were suspended in 60 ml of $THF/CH_2Cl_2$ (1:1) and adjusted to pH 8.5 by the addition of about 0.7 ml of Hünig base. 0.77 g of TBTU were added and the mixture was stirred overnight at room temperature. The clear reaction solution was evaporated down in vacuo, the residue was taken up in $CH_2Cl_2$ and extracted twice with 10% $KHSO_4$ solution, once with saturated NaCl solution, twice with 10% $KHCO_3$ solution and once more with saturated NaCl solution. The organic phase was dried over $Na_2SO_4$, filtered and evaporated down, whereupon crystallisation took place. 0.685 g of (R,S)-1-cyclohexyl-piperazinyl-4-[2-phenylacetic acid-N-(3,5-bis-trifluoromethylbenzyl)amide] were obtained as a yellowish solid. Yield 64%.

Mp: 124–129° C. FAB-MS: $(M+H)^+=528.2$.

EXAMPLE 2

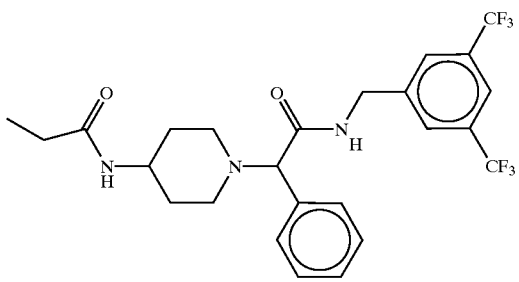

1st Step: 0.49 g of 3,5-bis-(trifluoromethyl)-benzylamine were dissolved in 30 ml of anhydrous $CH_2Cl_2$, 0.3 ml of triethylamine were added, the mixture was cooled in an ice bath and over 20 minutes a solution of 0.46 g of (R,S)-α-bromophenylacetyl chloride in 10 ml of $CH_2Cl_2$ was added dropwise. After the mixture had stood at room temperature over a weekend, the solvent was eliminated and the solid residue was triturated with diethylether, suction filtered and the filtrate was evaporated down. 0.6 g of α-bromophenylacetic acid N-(bis-trifluoromethylbenzyl)-amide were obtained as a light beige solid.

Yield: 43.5%.

2nd Step: 0.21 g of 4-propionylamino-piperidine hydrochloride were dissolved in 30 ml of anhydrous DMF, 0.33 g of $K_2CO_3$ were added and the mixture was stirred for 30 minutes at room temperature. Over 20 minutes a solution of 0.68 g of the product of the first step in 10 ml of DMF were added dropwise to this mixture, which was then stirred overnight at room temperature. The suspension was filtered, the filtrate was evaporated down, the oily residue obtained was taken up in ethyl acetate, extracted twice with 10% $KHCO_3$ solution and once with saturated NaCl solution. The organic phase was dried over $Na_2SO_4$, filtered, the filtrate was evaporated down and the semi-solid residue obtained was triturated with diethylether and suction filtered. 0.33 g of (R,S)-4-propionylamino-1-[2-phenylacetic acid-N(3,5-bis-trifluoromethyl-benzyl)-amide]-piperidine were obtained as a white solid.

Yield: 64%. Mp: 189–191° C. FAB-MS: (M+H)$^+$=516.4.

EXAMPLE 33

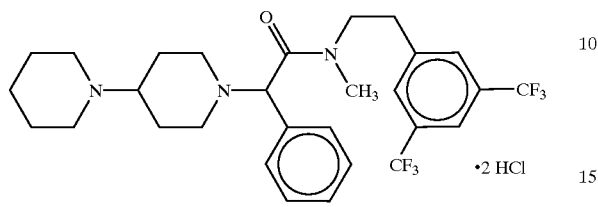

Mp: >240° C.; FAB-MS: (M+H)$^+$=556.4

0.3 g of the compound according to Example 25 were converted into the corresponding base by treatment with KHCO$_3$ and dried. The resulting product was dissolved in 5 ml of anhydrous THF, 34 mg of NaH (60% in oil) were added and the mixture was stirred for 1.5 hours at room temperature. Then 0.1 g of methyliodide were added and the mixture was stirred overnight. The reaction mixture was mixed with 2 ml of THF/water (1:1) then with 25 ml of water and extracted 3 times with ether. The combined ether extracts were dried over Na$_2$SO$_4$ and evaporated down in vacuo, thereby obtained 170 mg of the desired compound in the form of a free base (oil). This was converted into the dihydrochloride by the addition of an excess of ethereal HCl, the dihydrochloride being obtained in the form of yellow crystals.

Yield: 113 mg (36%).

The other compounds of the invention may be prepared analogously, e.g. as follows:

EXAMPLE 3

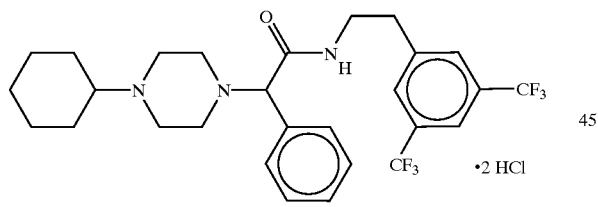

Mp 235–238° C. FAB-MS: (M+H)$^+$=542.2.

EXAMPLE 4

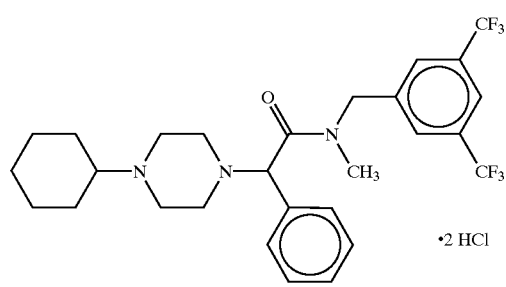

Mp: >240° C. (Decomp.). FAB-MS: (M+H)$^+$=542.3.

EXAMPLE 5

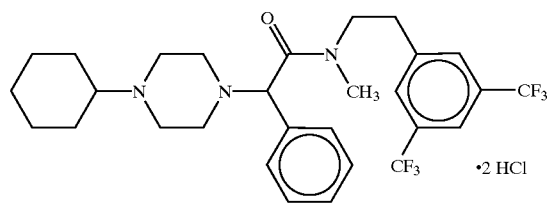

Mp: 158–164° C.; FAB-MS: (M+H)$^+$=556.4.

EXAMPLE 6

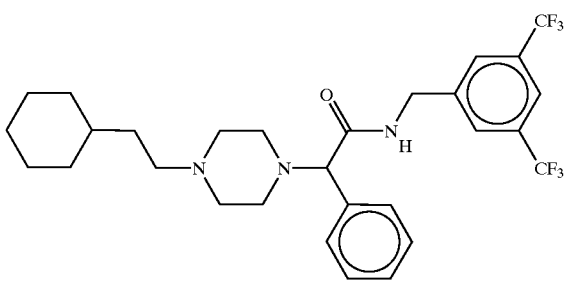

Mp: 97–99° C.; FAB-MS: (M+H)$^+$=556.3.

EXAMPLE 7

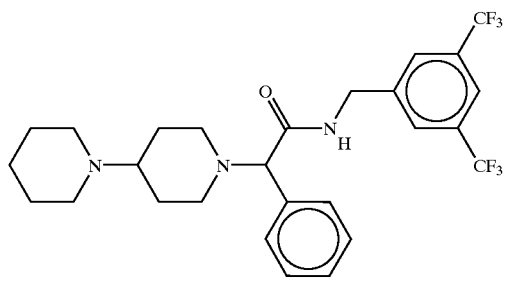

Mp: >240° (Decomp.); FAB-MS: (M+H)$^+$=528.4.

EXAMPLE 8

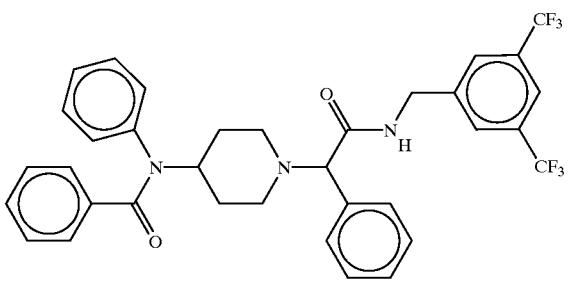

Mp: 102–105° C.; FAB-MS: (M+H)$^+$=640.3.

EXAMPLE 9
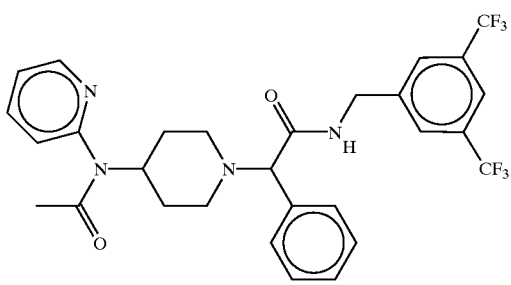
Mp: 141–149° C.; FAB-MS: (M+H)⁺=579.2.
EXAMPLE 10
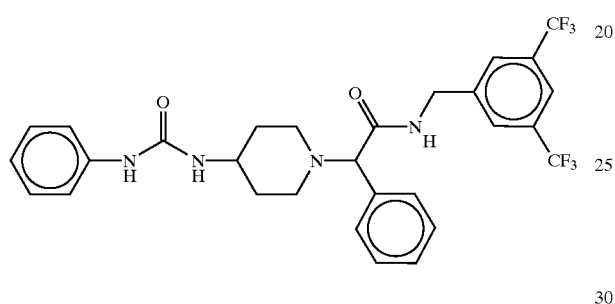
Mp: 218–223° C.; FAB-MS: (M+H)⁺=579.3.
EXAMPLE 11
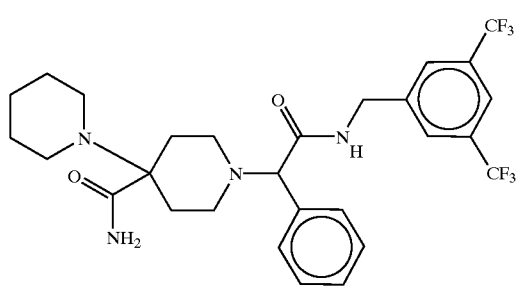
Mp: >220° (Decomp.); FAB-MS (M+H)⁺=571.3
EXAMPLE 12
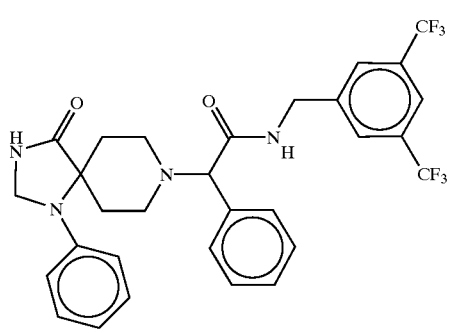
Mp: 205–210° C.; FAB-MS: (M+H)⁺=591.3.
EXAMPLE 13
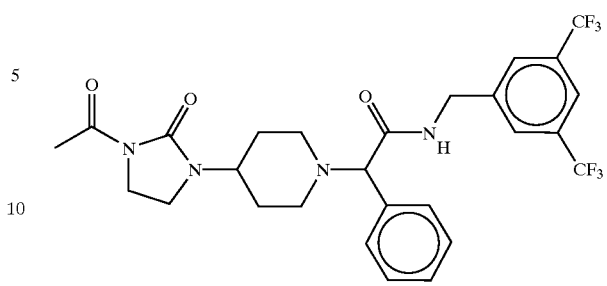
Mp: 87–95° C.; FAB-MS: (M+H)⁺=571.2
EXAMPLE 14
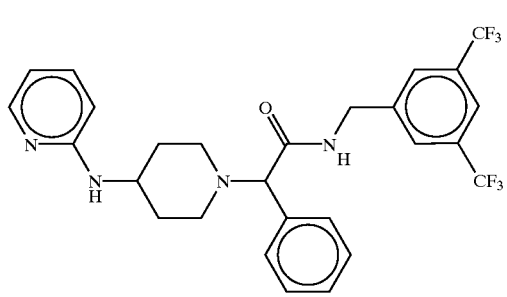
Mp: 164–166° C.; FAB-MS: (M+H)⁺=537.3.
EXAMPLE 15
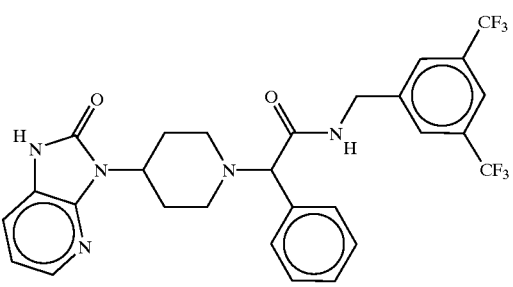
Mp: 208–210° C.; FAB-MS: (M+H)⁺=578.3.
EXAMPLE 16
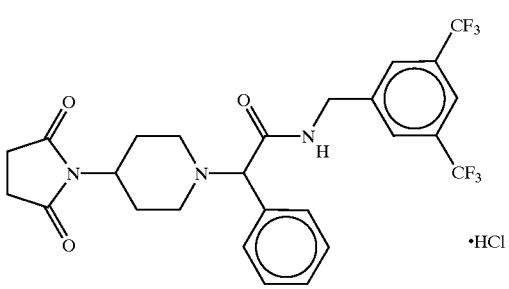
Mp: 110–115° C.; FAB-MS: (M+H)⁺=542.3.

EXAMPLE 17
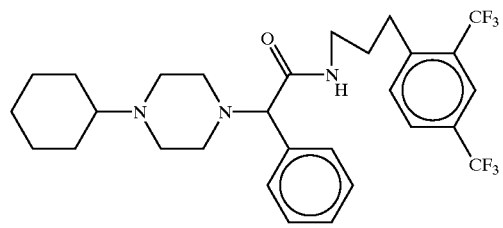
Mp: 118–123° C.; FAB-MS: (M+H)$^+$=556.3
EXAMPLE 18
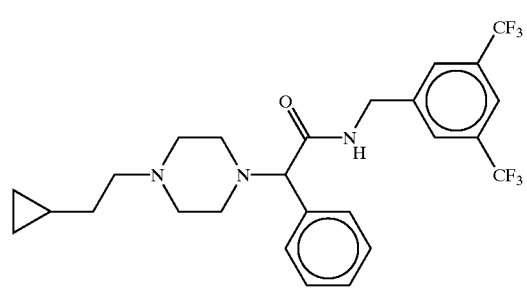
Mp: 134–136° C.; FAB-MS: (M+H)$^+$=514.3
EXAMPLE 19
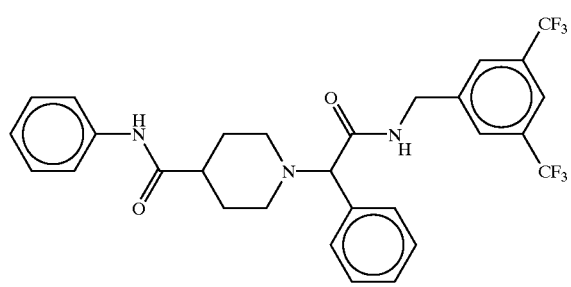
Mp: >240° (Decomp.): FAB-MS: (M+H)$^+$=564
EXAMPLE 20
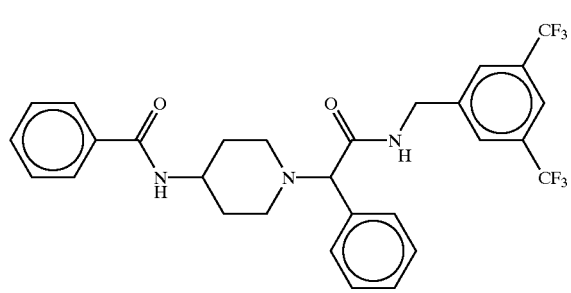
Mp: 180–185° C.; FAB-MS: (M+H)$^+$=564.3
EXAMPLE 21
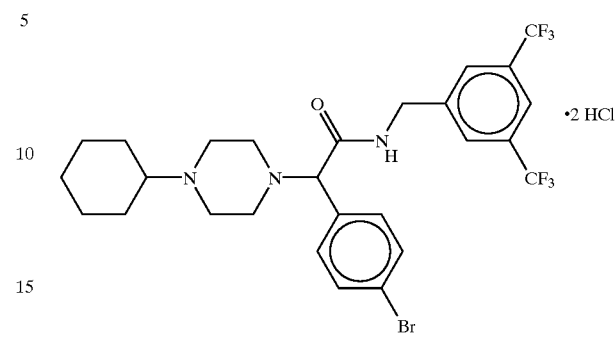
Mp: 228–232° C.; FAB-MS: (M+H)$^+$=606/608
EXAMPLE 22
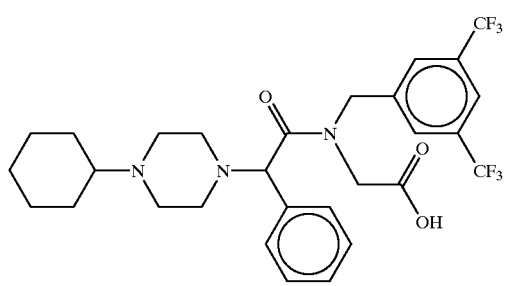
Mp: 70–73° C.; FAB-MS: (M+H)$^+$=586
EXAMPLE 23
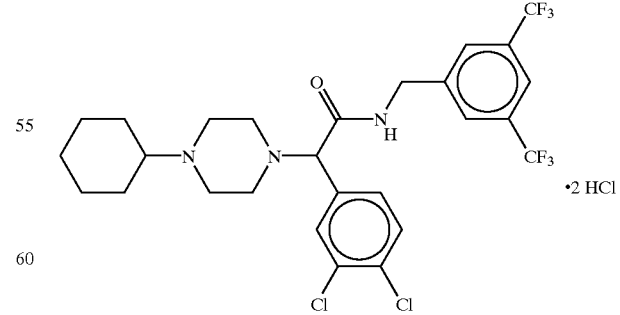
Mp: 248–254° C.; FAB-MS: (M+H)$^+$=596/598/600

EXAMPLE 24
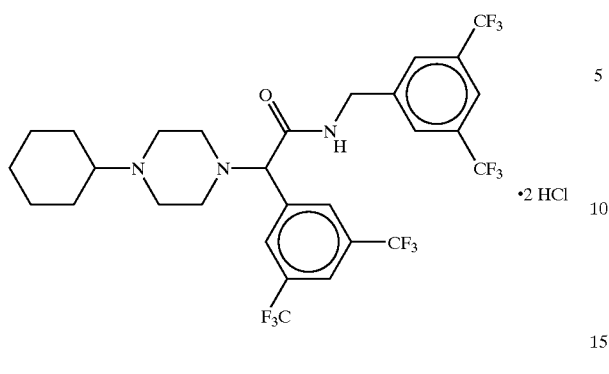
Mp: 210° C.; FAB-MS: (M+H)⁺=664.1
EXAMPLE 25
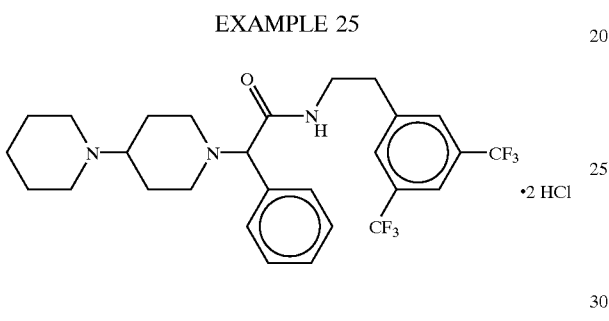
Mp: 192–199° C.; FAB-MS: (M+H)⁺=542.3
EXAMPLE 26
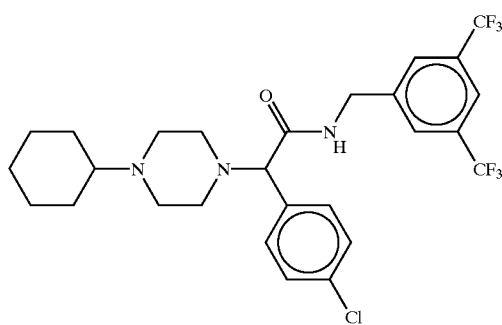
Mp: 112–118° C.; FAB-MS: (+H)⁺=562/564
EXAMPLE 27
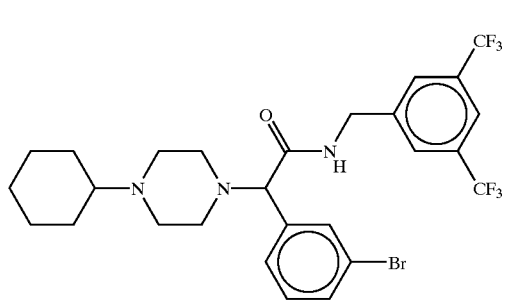
Mp: 124–127° C.; FAB-MS: (M+H)⁺=606/608
EXAMPLE 28
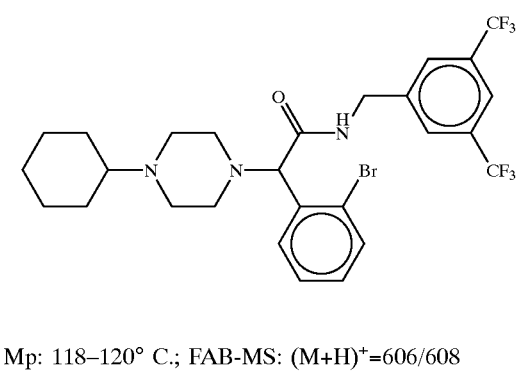
Mp: 118–120° C.; FAB-MS: (M+H)⁺=606/608
EXAMPLE 29
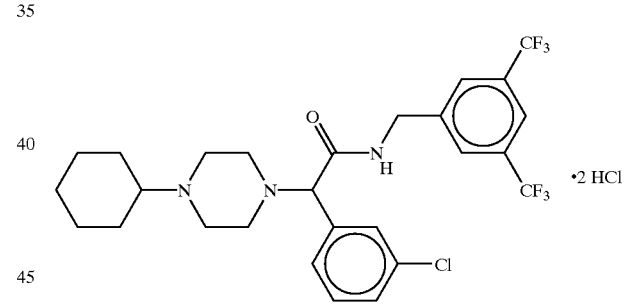
Mp: 120–122° C.; FAB-MS: (M+H)⁺=562/564
EXAMPLE 30
Mp: >240° C.; FAB-MS: (M+H)⁺=562/564
EXAMPLE 31
Mp: >240° C.; FAB-MS: (M+H)⁺=546.3

EXAMPLE 32
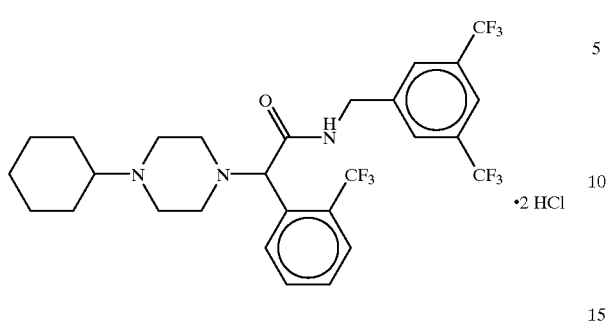
Mp: 125–130° C. (Decomp); FAB-MS: (M+H)⁺=610.4
EXAMPLE 33
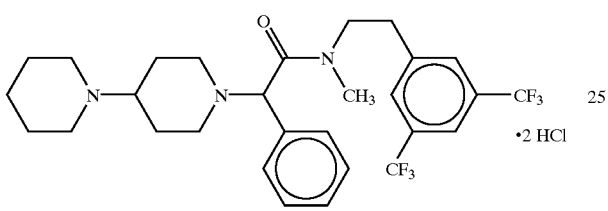
Mp: >240° C.; FAB-MS: (M+H)⁺=556.4
EXAMPLE 34
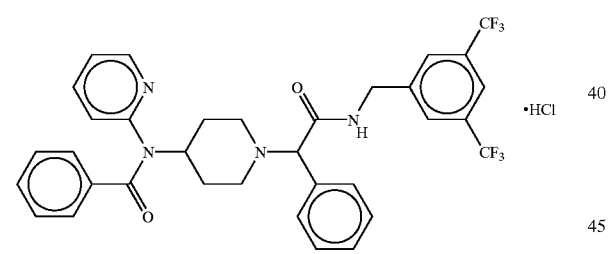
Mp: 145–151° C.; FAB-MS: (M+H)⁺=641.3
EXAMPLE 35
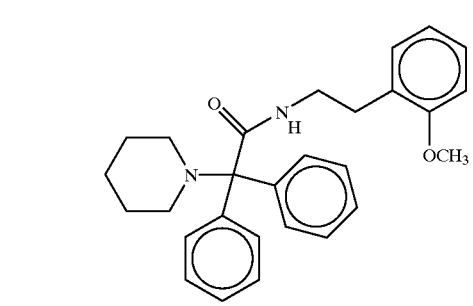
EXAMPLE 36
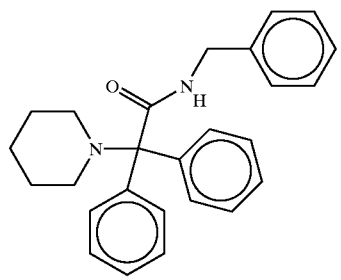
Mp: 175–176.5° C.
EXAMPLE 37
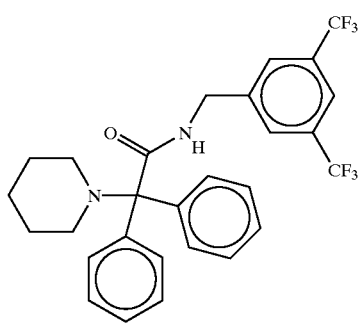
Mp: 157–158° C.
EXAMPLE 38
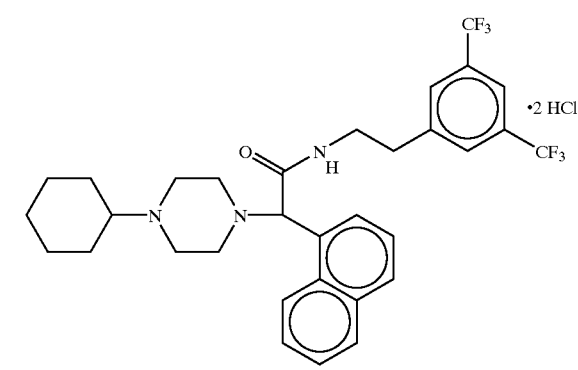
Mp: 155–172° C. FAB-MS: (M+H)⁺=592.2

EXAMPLE 39
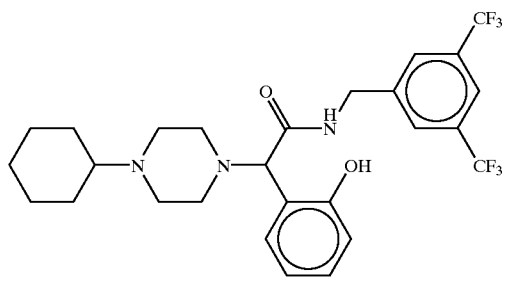
EXAMPLE 40
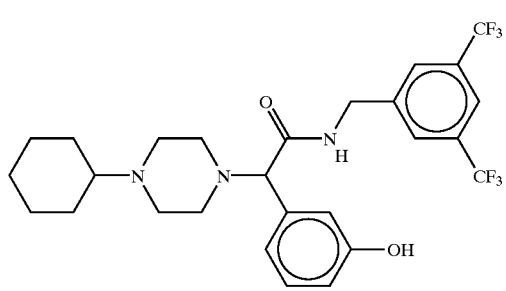
EXAMPLE 41
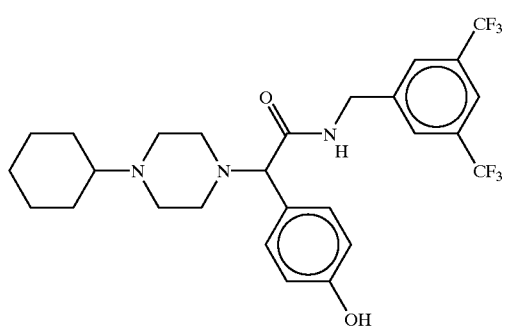
EXAMPLE 42
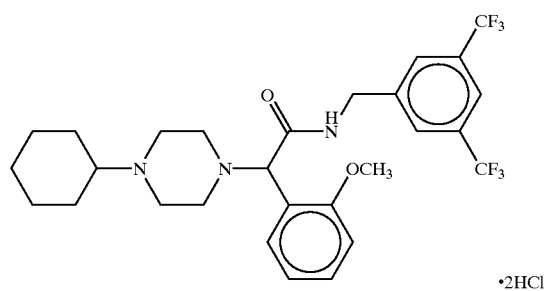
Mp: 142–150° C. FAB-MS: $(M+H)^+=558.2$
EXAMPLE 43
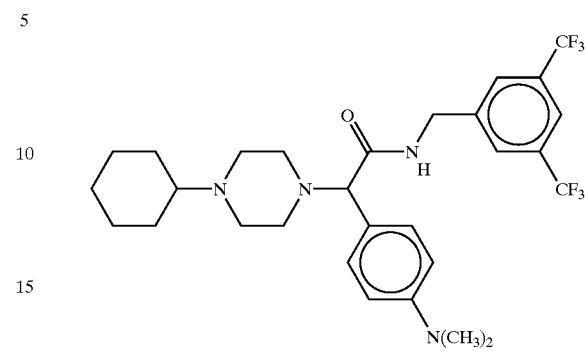
EXAMPLE 44
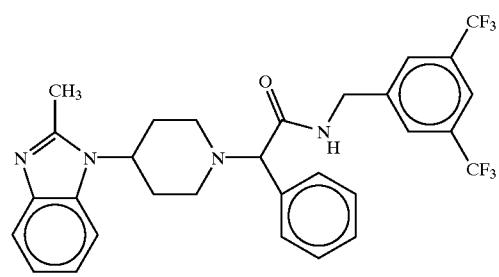
Mp: 107–111° C.; FAB-MS: $(M+H)^+=575.6$
EXAMPLE 45
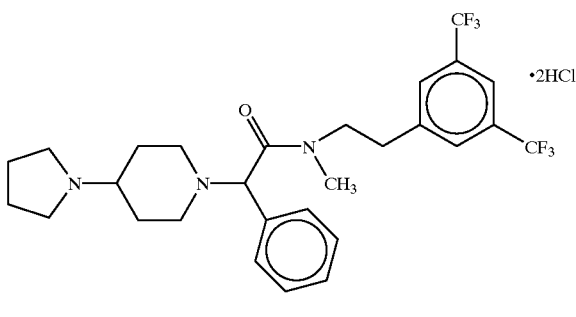
M.p: >230° C.

EXAMPLE 46
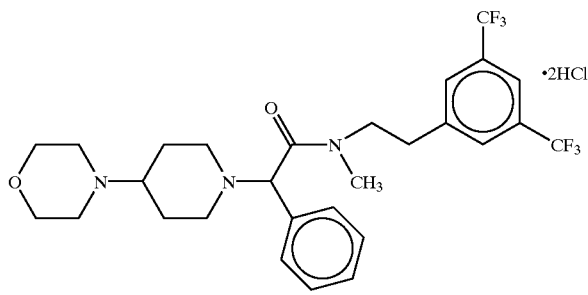
M.p: >230° C.
EXAMPLE 47
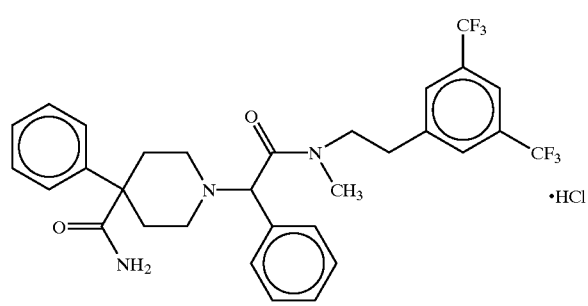
M.p: 127–137° C. FAB-MS: (M+H)⁺=592
EXAMPLE 48
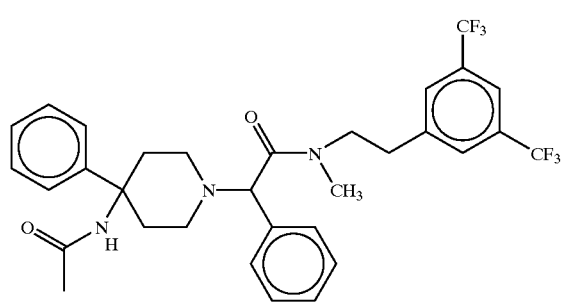
EXAMPLE 49
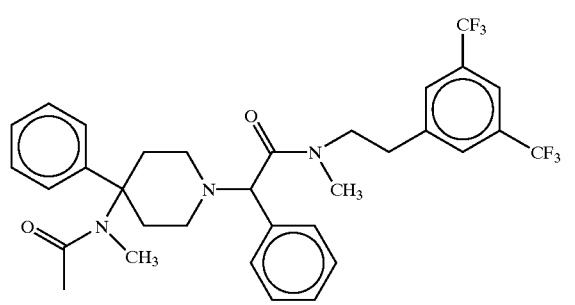
EXAMPLE 50
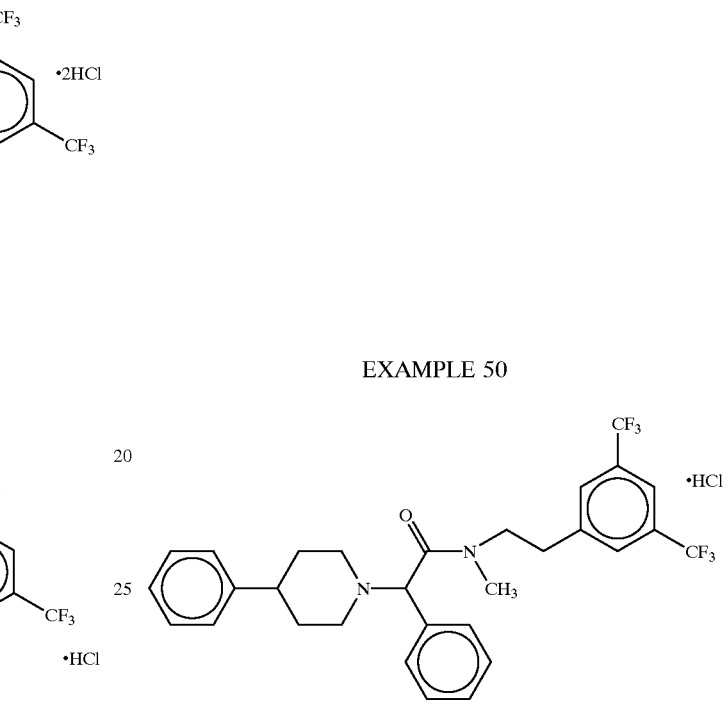
M.p. 106–110° C. FAB-MS: (M+H)⁺=549.4
EXAMPLE 51
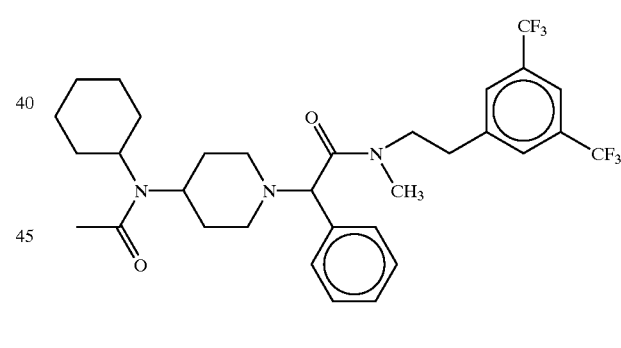
EXAMPLE 52
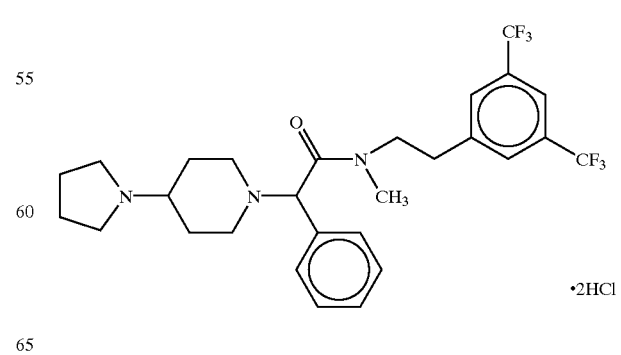
Mp: 133–143° C. FAB-MS: (M+H)⁺=542.3

EXAMPLE 53
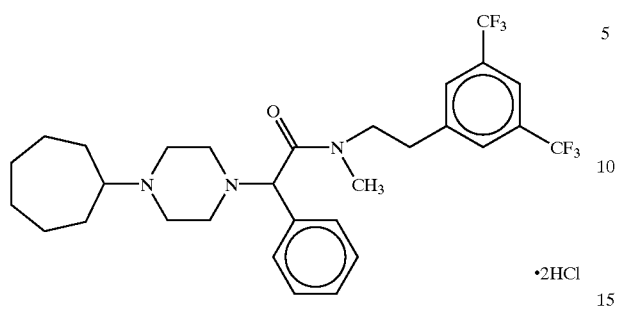
M.p. 110–120° C. FAB-MS: (M+H)⁺=570.4
EXAMPLE 54
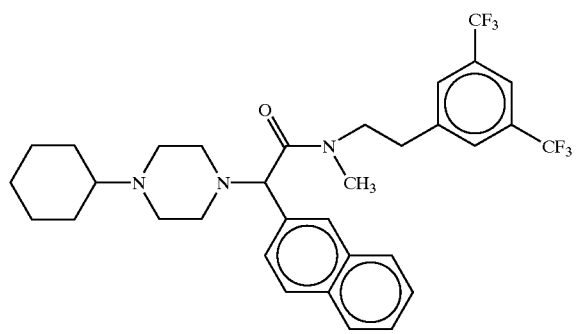
EXAMPLE 55
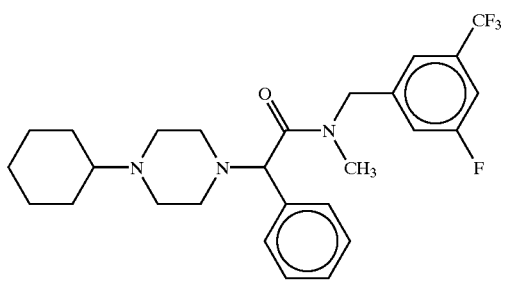
EXAMPLE 56
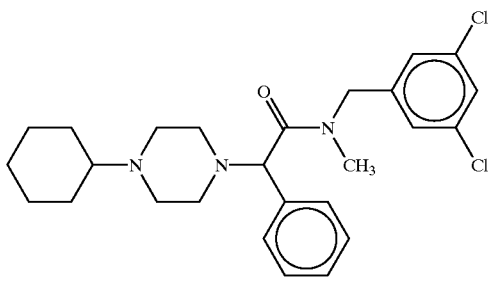
EXAMPLE 57
(structure shown above)
EXAMPLE 58
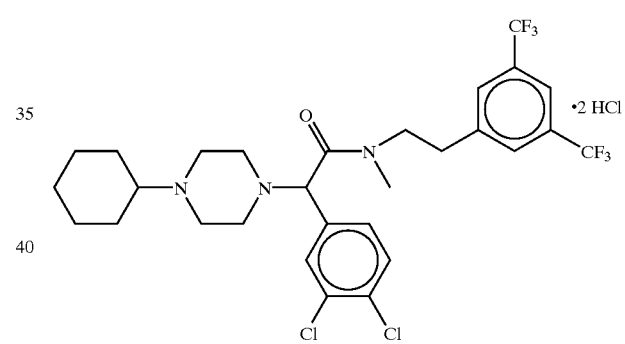
Mp: 212–216° C. (Decomp.) FAB-MS: (M+H)⁺=624.3/626.3/628.3
EXAMPLE 59
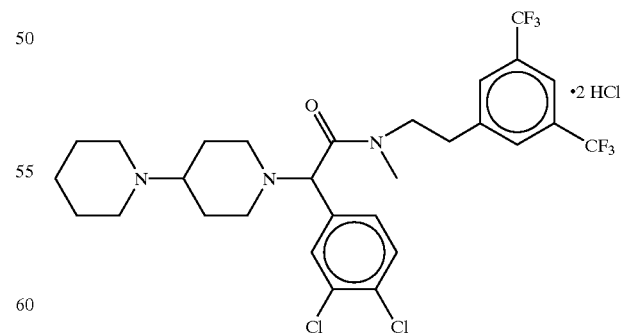
Mp: 244–246° C. (Decomp.) FAB-MS: (M+H)⁺=624.1/626.2/628

EXAMPLE 60
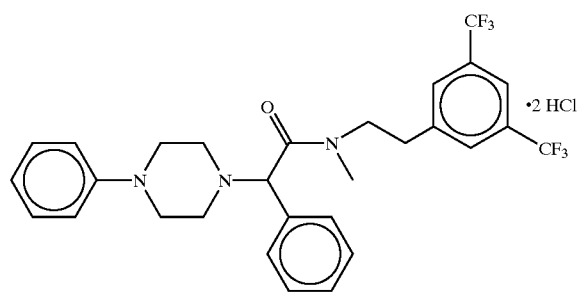
Mp: 113–123° C. FAB-MS: (M+H)⁺=550.3
EXAMPLE 61
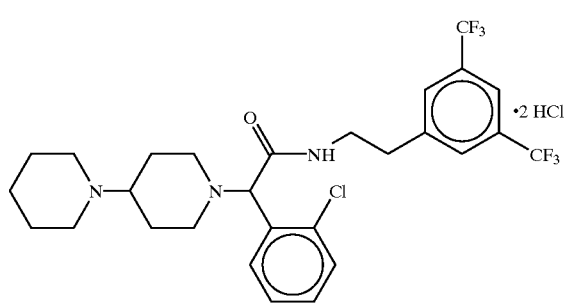
Mp: 195–205° C.
EXAMPLE 62
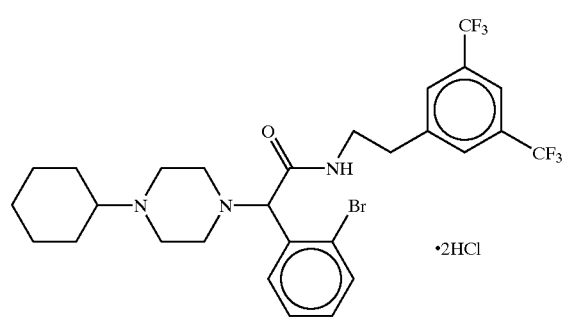
Mp: 210–218° C. FAB-MS: (M+H)⁺=620/622
EXAMPLE 63
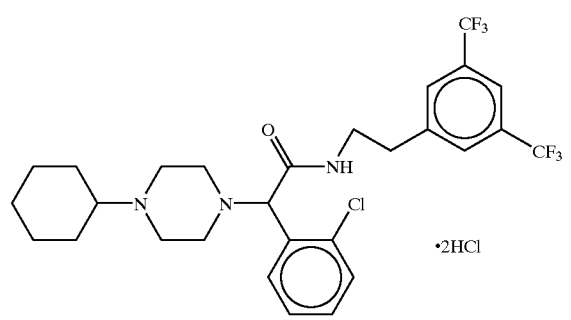
Mp: 215–224° C. FAB-MS: (M+H)⁺=576/578
EXAMPLE 64
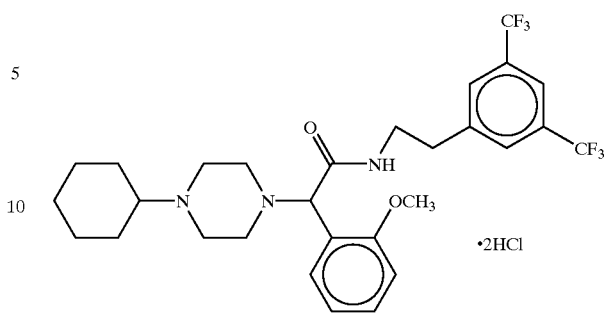
Mp: 85–92° C. FAB-MS: (M+H)⁺=572.5
EXAMPLE 65
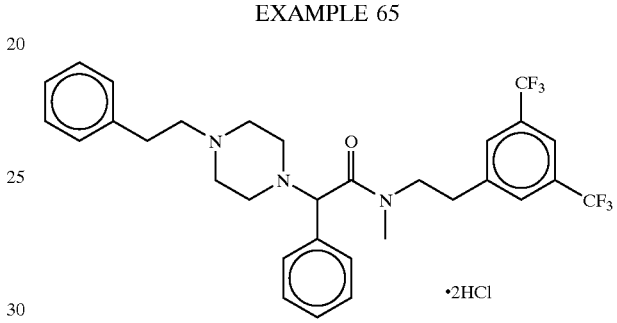
Mp: 148–156° C. FAB-MS: (M+H)⁺=578.4
EXAMPLE 66
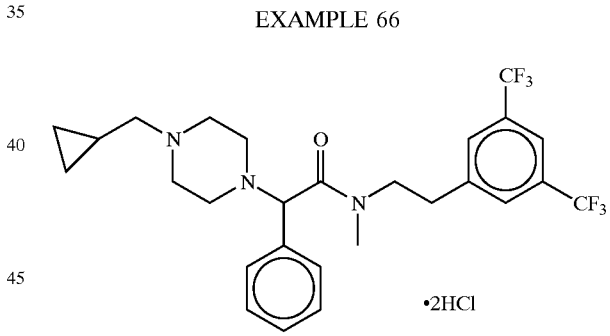
Mp: 113–117° C. (decomp.) FAB-MS: (M+H)⁺=528.5
EXAMPLE 67
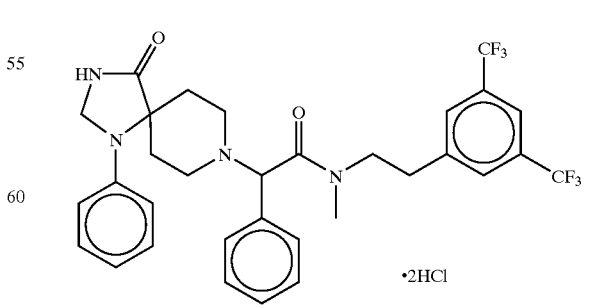
Mp: 265–268° C. (decomp.) FAB-MS: (M+H)⁺=619.3

EXAMPLE 68
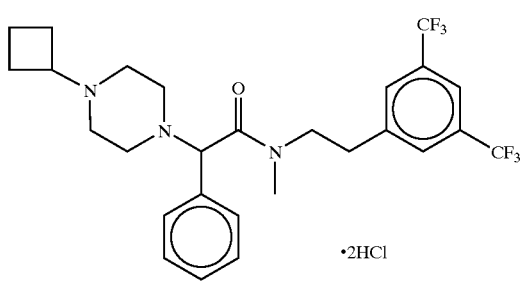
•2HCl
Mp: 236–238° C. (decomp.) FAB-MS: (M+H)⁺=528.3
EXAMPLE 69
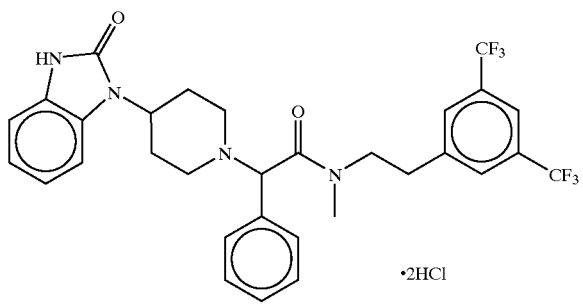
•2HCl
Mp: 177–187° C. FAR-MS: (M+H)⁺=605.3
EXAMPLE 70
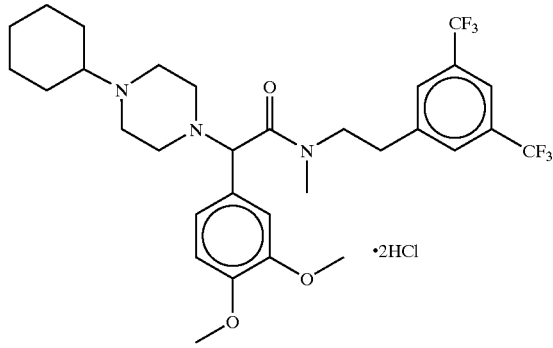
•2HCl
Mp: 123–133° C. (decomp.) FAB-MS: (M+H)⁺=616.3
EXAMPLE 71
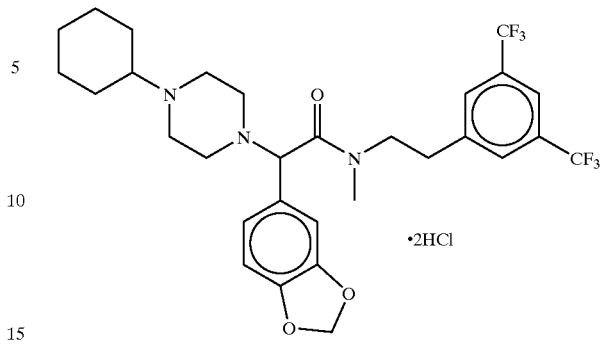
•2HCl
Mp: 87–97° C. FAB-MS: (M+H)³⁰ =600.2
EXAMPLE 72
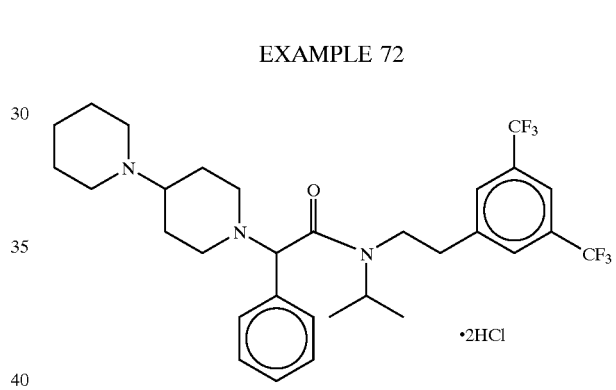
•2HCl
Mp: >230° C.
EXAMPLE 73
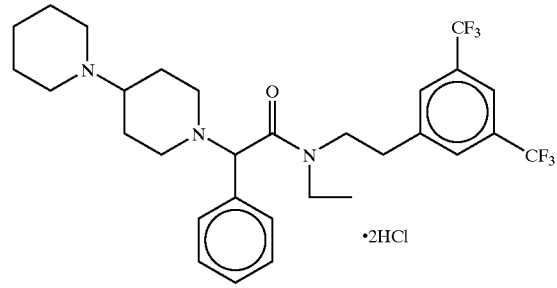
•2HCl
Mp: >230° C.

EXAMPLE 74

Mp: >230° C.

EXAMPLE 75

Mp: 91–98° C. FAB-MS: (M+H)$^+$=574.4

EXAMPLE 76

Mp: 234–236° C.

EXAMPLE 77

Mp: 195–198° C.

EXAMPLE 78

Pharamaceutical Preparations

| Injectable solution | | |
|---|---|---|
| 200 mg | of active substance* | |
| 1.2 mg | of monopotassium dihydrogen phospate = KH$_2$PO$_4$ | ) |
| 0.2 mg | of disodium hydrogen phosphate = NaH$_2$PO$_4$.2H$_2$O | ) (buffer) ) |
| 94 mg or | of sodium chloride | ) ) (isotonic) |
| 520 mg | of glucose | ) |
| 4 mg | of albumin (protease protection) | |
| q.s. | sodium hydroxide solution | ) |
| q.s. | hydrochloric acid | ) to adjust the pH to pH 6 | sufficient water to make a 10 ml solution for injection

| Injectable solution | | |
|---|---|---|
| 200 mg | of active substance* | |
| 94 mg or | of sodium chloride | |
| 520 mg | of glucose | |
| 4 mg | of albumin | |
| q.s. | sodium hydroxide solution | ) |
| q.s. | hydrochloric acid | ) to adjust the pH to pH 9 | sufficient water to make a 10 ml solution for injections

| Lyophilisate | |
|---|---|
| 200 mg | of active substance* |
| 520 mg | of mannitol (isotonic/structural component) |
| 4 mg | of albumin |
| Solvent 1 for lyophilisate | |
| 10 ml | of water tor injections |
| Solvent 2 for lyophilisate | |
| 20 mg | of Polysorbate ® 80 = Tween ® 80 (surfactant) |
| 10 ml | of water for injections |

*Active substance: compound according to the invention, e.g. that of Examples 1 to 78.

Dosage for humans weighing 67 kg: 1 to 500 mg

What is claimed is:
1. A method of treatment of depression in a patient comprising administering to said patient in need of such treatment an effective amount of a compound of formula I:

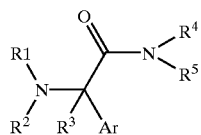
(I)

or a pharmaceutically acceptable salt thereof, wherein

Ar is unsubstituted or mono- to penta-substituted phenyl, or unsubstituted or mono- or di-substituted naphthyl, in which the substituents of the phenyl and naphthyl are independently selected from the group consisting of halogen, hydroxy, $(C_{1-4})$alkyl, $O-(C_{1-4})$alkyl, $CF_3$, $OCF_3$ and $NR^9R^{10}$, wherein $R^9$ and $R^{10}$ are independently selected from the group consisting of hydrogen, methyl and acetyl; or Ar is phenyl substituted by $-O-CH_2-O-$ or $-O-(CH_2)_2-O-$;

$R^1$ and $R^2$ together with the N to which they are bound form a ring of the formula

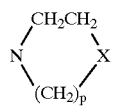

wherein p is 2 or 3; and

X is oxygen; or

X is $N(CH_2)_nR^6$; wherein n is 0, 1 or 2, and $R^6$ is $(C_{3-7})$cycloalkyl, phenyl or naphthyl, wherein the phenyl is optionally mono- to tri-substituted by halogen, $(C_{1-4})$alkyl, $O-(C_{1-4})$alkyl, $CF_3$, $OCF_3$ or $NR^9R^{10}$, wherein $R^9$ and $R^{10}$ are independently selected from the group consisting of hydrogen, methyl and acetyl; or X is $CR^7R^8$, wherein $R^7$ and $R^8$ have one of the following meanings:

(a) $R^7$ and $R^8$ are each hydrogen when $R^3$ is unsubstituted or substituted phenyl;

(b) $R^7$ is phenyl, phenyl substituted by 1 to 3 substituents, wherein the substituents are independently selected from the group consisting of halogen, $(C_{1-4})$ alkyl, $O-(C_{1-4})$ alkyl, $CF_3$ and $OCF_3$, piperidinyl, 1-methylpiperidinyl,

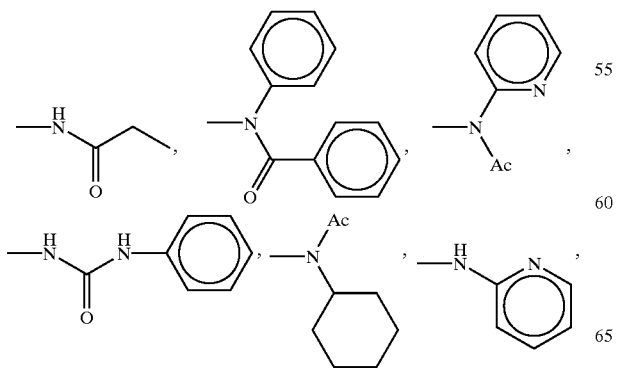

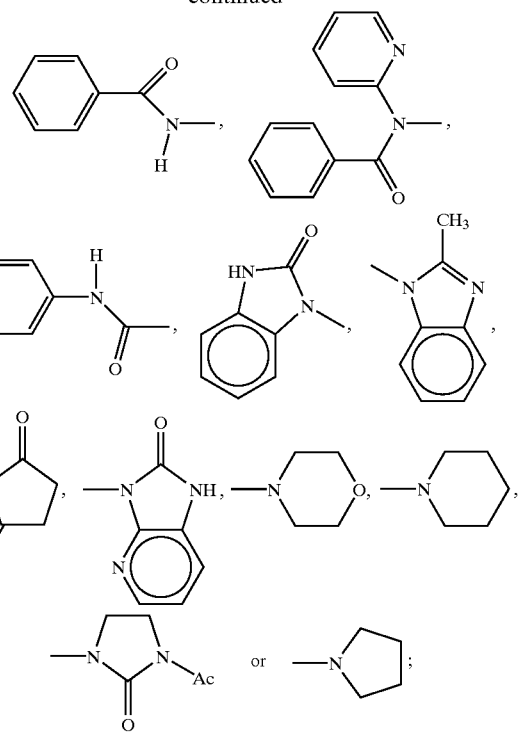

when $R^8$ is hydrogen, $-CONH_2$, $-NHC(O)CH_3$, $-N(CH_3)C(O)CH_3$, CN, $-C(O)NH(C_{1-3})$alkyl, or $-C(O)N((C_{1-3})$alkyl$)_2$; or (c) $R^7$ and $R^8$ together form the group

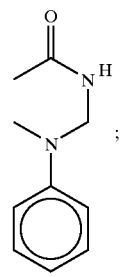

$R^3$ is hydrogen, $(C_{1-4})$alkyl, unsubstituted phenyl or mono- to tri-substituted phenyl, wherein the substituents are independently selected from the group consisting of halogen, $(C_{1-4})$alkyl, $O-(C_{1-4})$alkyl, $CF_3$, $OCF_3$ and $NR^9R^{10}$, wherein $R^9$ and $R^{10}$ are independently selected from the group consisting of hydrogen, methyl and acetyl;

$R^4$ is phenyl $(C_{1-4})$alkyl or naphthyl $(C_{1-4})$alkyl, wherein phenyl is optionally substituted by 1 to 3 substituents, independently selected from the group consisting of halogen, $(C_{1-4})$alkyl, $O-(C_{1-4})$alkyl, $CF_3$, $OCF_3$ and $NR^9R^{10}$, wherein $R^9$ and $R^{10}$ are independently selected from the group consisting of hydrogen, methyl and acetyl; and $R^5$ is hydrogen, $(C_{1-4})$alkyl, $(C_{3-6})$cycloalkyl, $CH_2COOH$, $-CH_2C(O)NH_2$, hydroxy or phenyl $(C_{1-4})$alkyl.

2. The method of claim 1, wherein said compound is an NK-1 antagonist.

3. The method of claim 1, wherein said administering is orally administering.

4. The method of claim 1, wherein X is oxygen.

5. The method of claim 1, wherein X is $N(CH_2)_nR^6$.

6. The method of claim 5, wherein $R^6$ is phenyl or naphthyl.

7. The method of claim 6, wherein said compound is selected from the group consisting of:

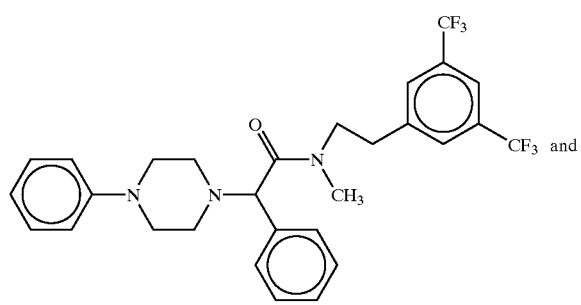

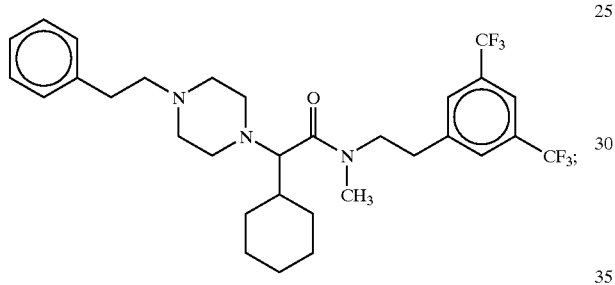

or a pharmaceutically acceptable salt thereof.

8. The method of claim 7, wherein said compound is selected from the group consisting of:

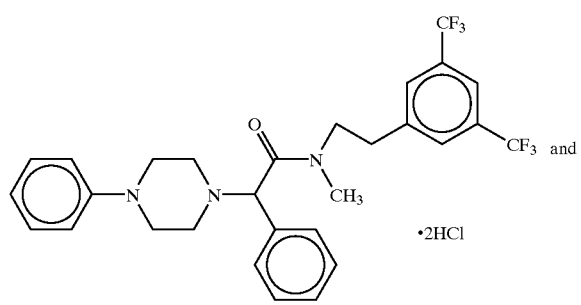

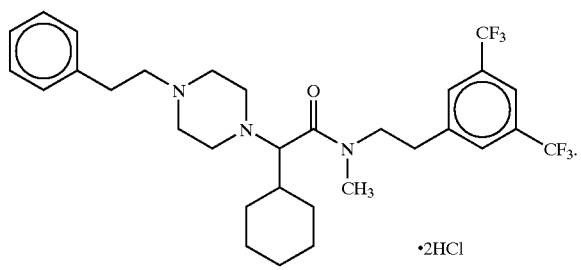

9. The method of claim 5, wherein $R^6$ is $(C_{3-7})$cycloalkyl.

10. The method of claim 9, wherein said compound is selected from the group consisting of:

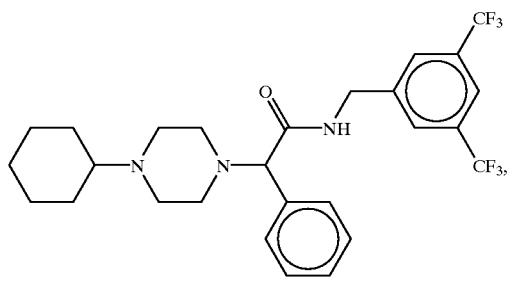

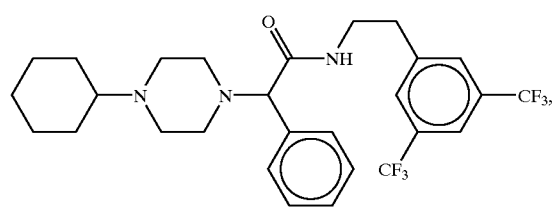

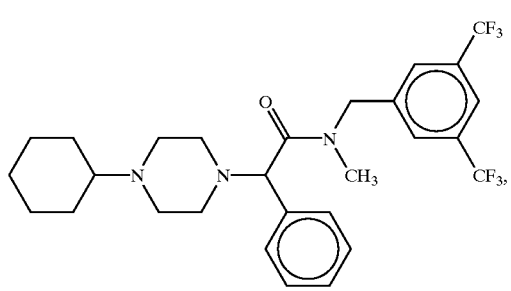

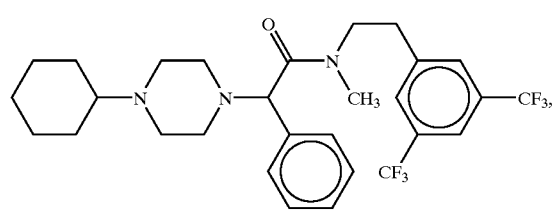

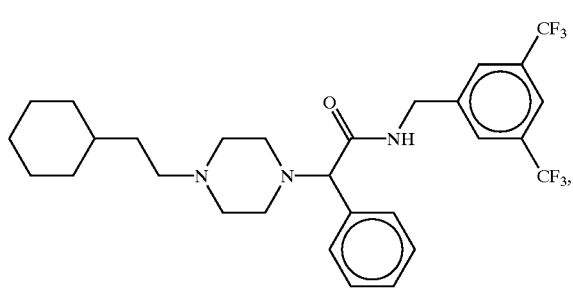

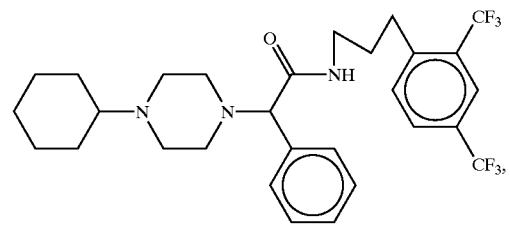
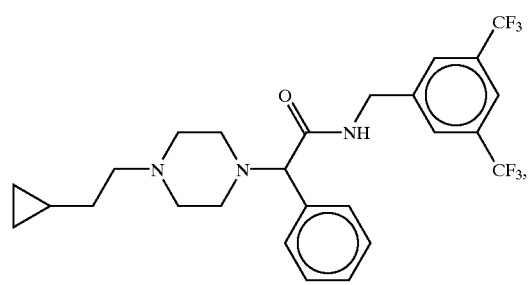
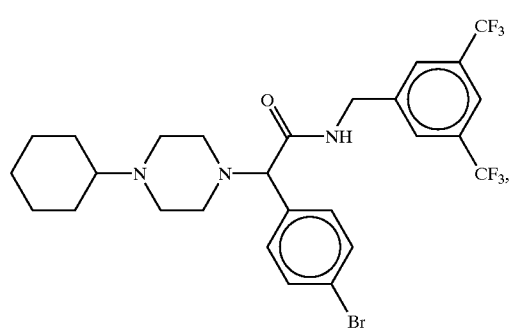
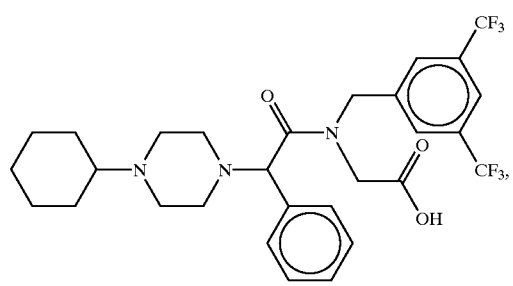
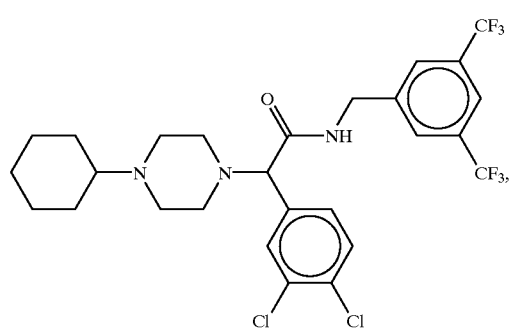
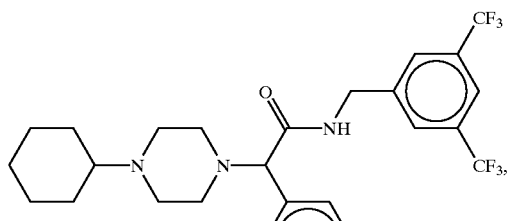
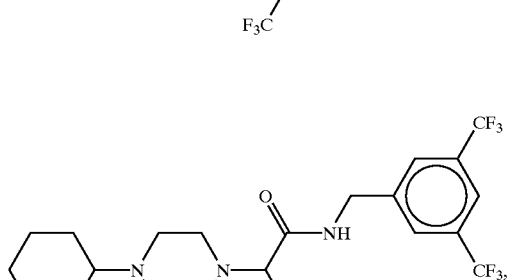
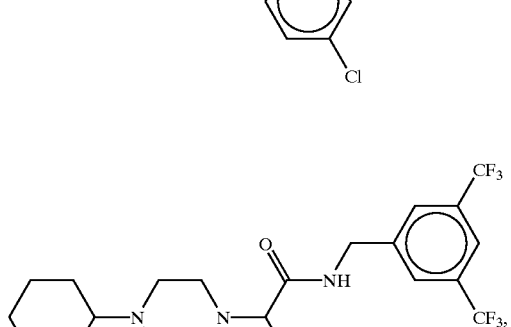
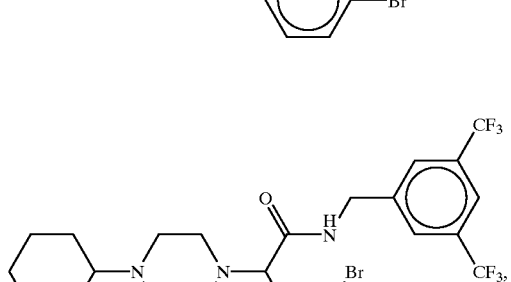
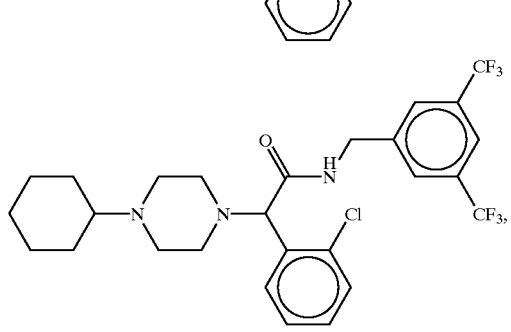

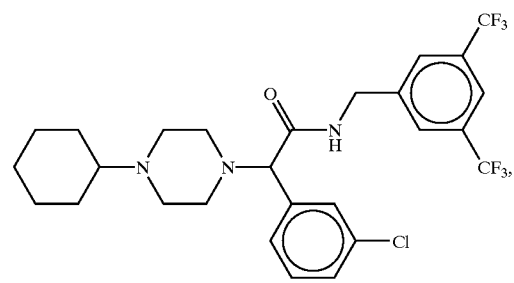
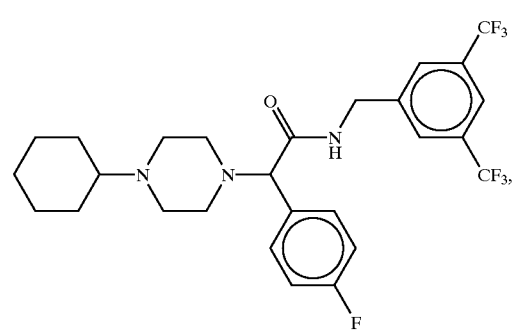
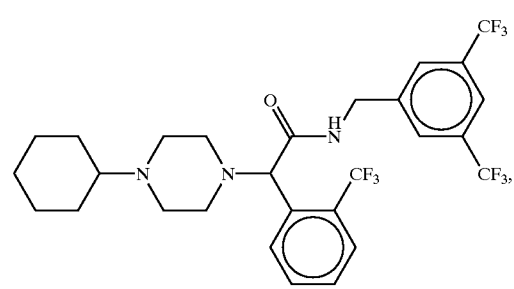
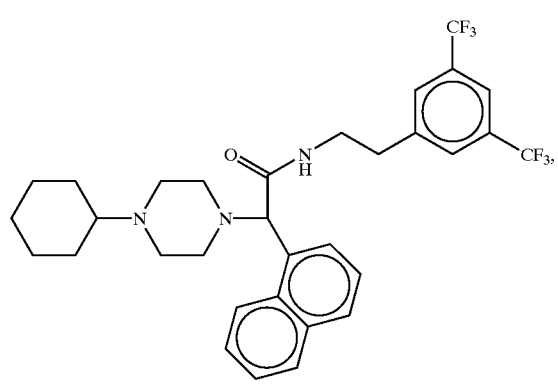
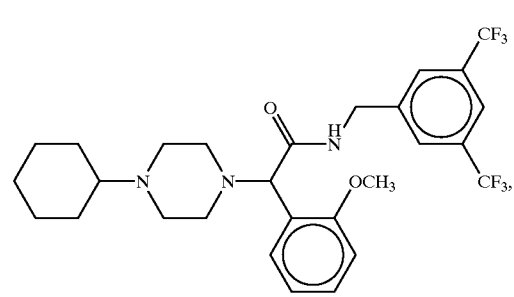
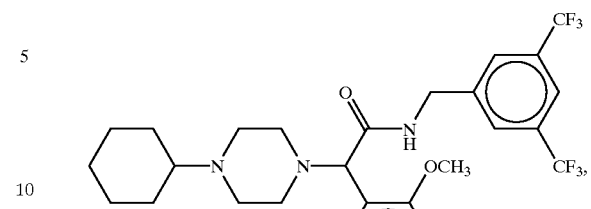
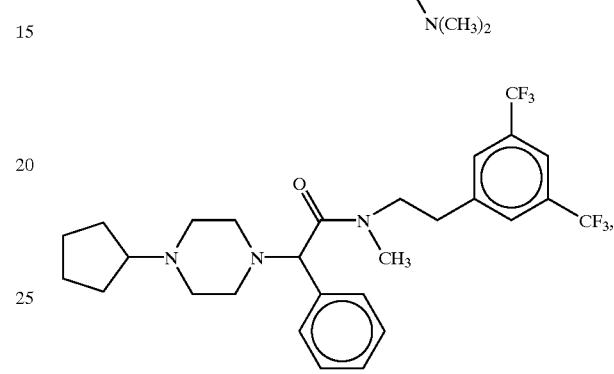
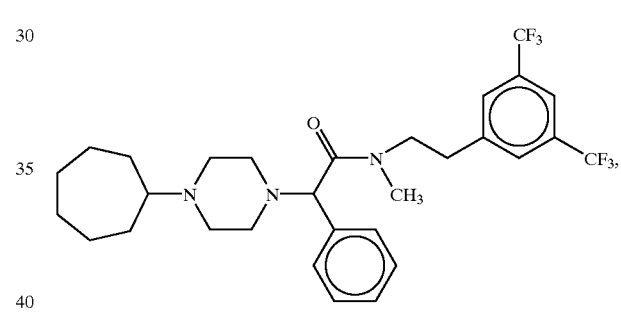
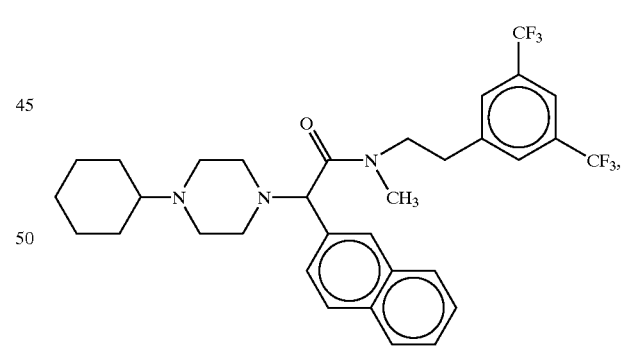
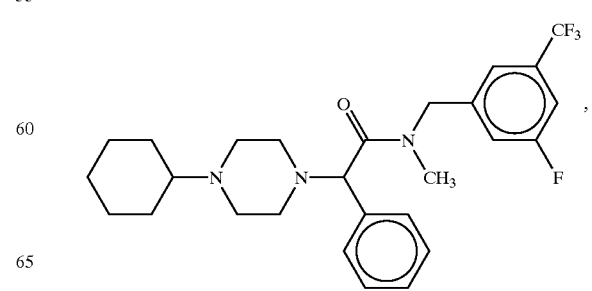

-continued

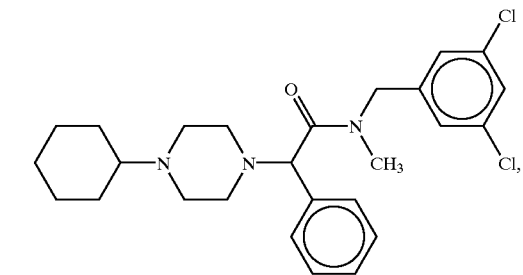

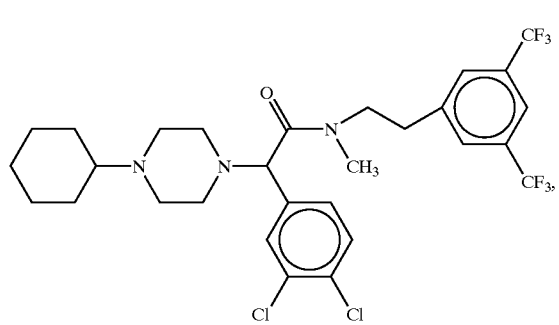

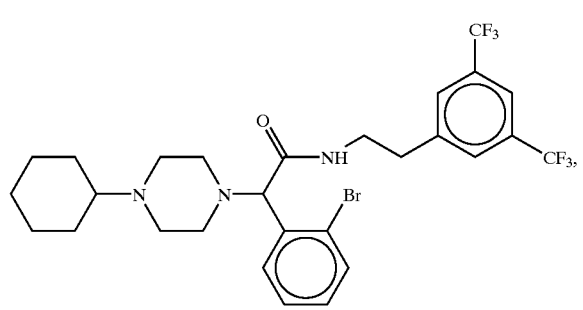

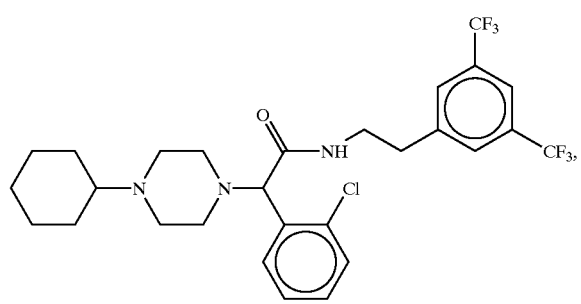

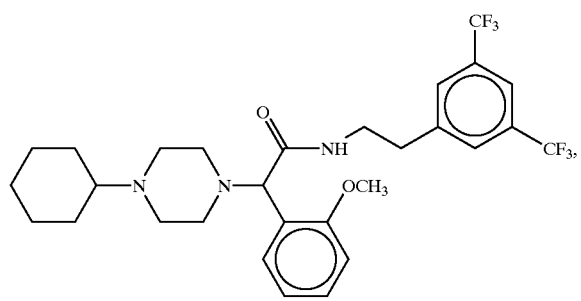

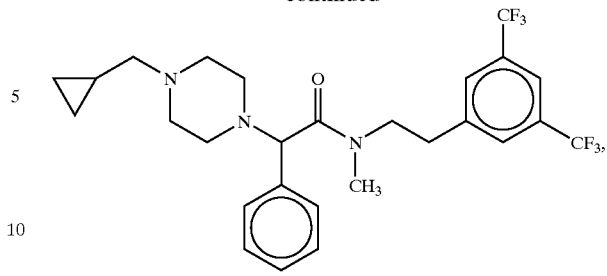

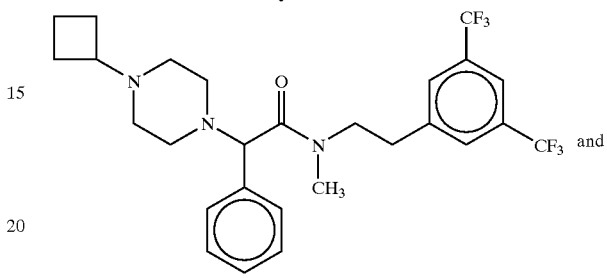

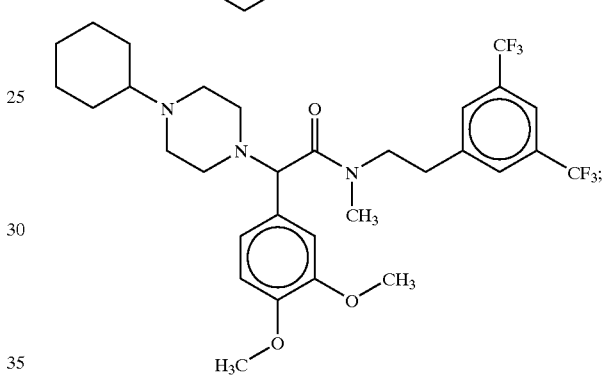

or a pharmaceutically acceptable salt thereof.

11. The method of claim 9, wherein said compound is:

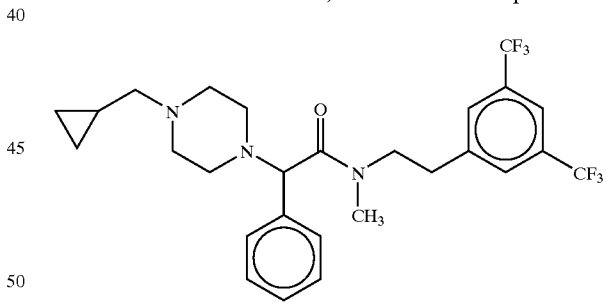

or a pharmaceutically acceptable salt thereof.

12. The method of claim 11, wherein said compound is a racemate.

13. The method of claim 11, wherein said compound is an enantiomer.

14. The method of claim 13, wherein said enantiomer is an (R)-enantiomer.

15. The method of claim 13, wherein said enantiomer is an (S)-enantiomer.

16. The method of claim 11, wherein said pharmaceutically acceptable salt is an HCl salt.

17. The method of claim 10, wherein said compound is selected from the group consisting of:

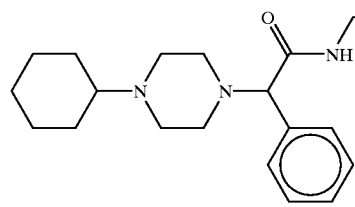
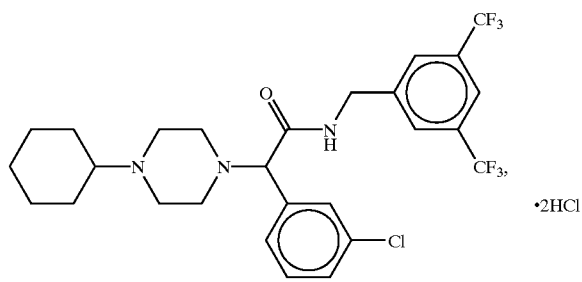
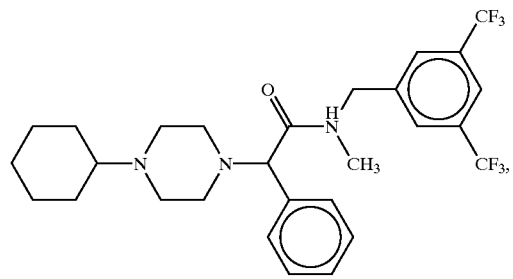
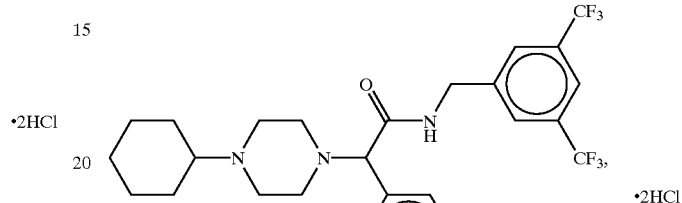
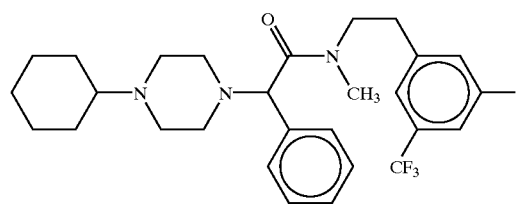
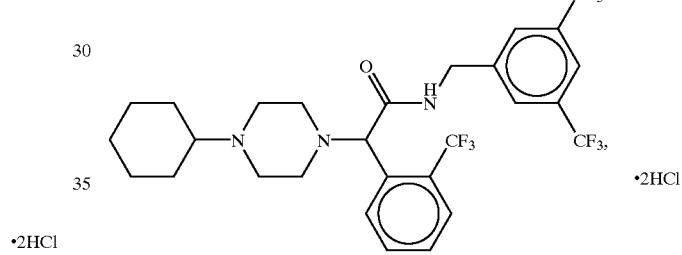
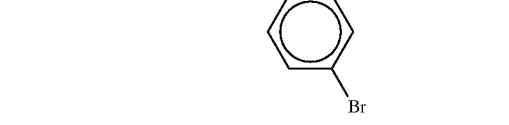
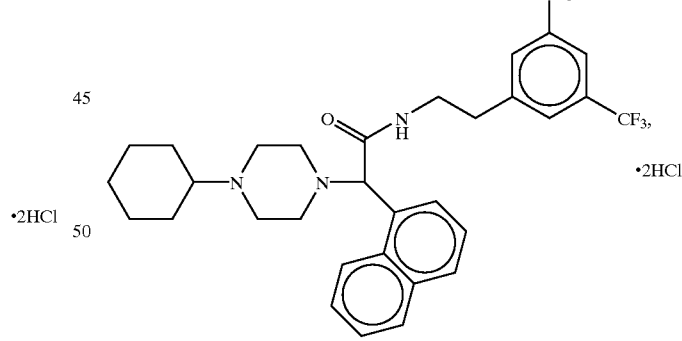
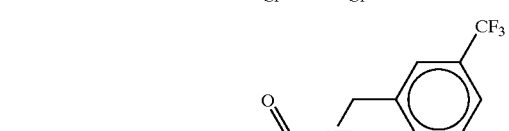
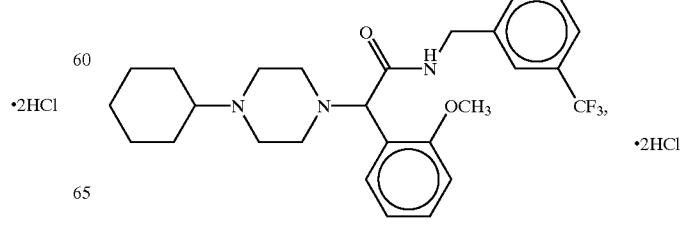

-continued
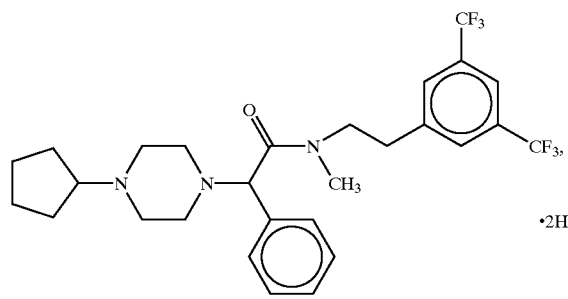
•2HCl
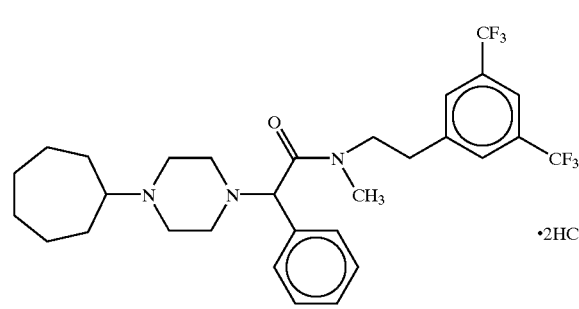
•2HCl
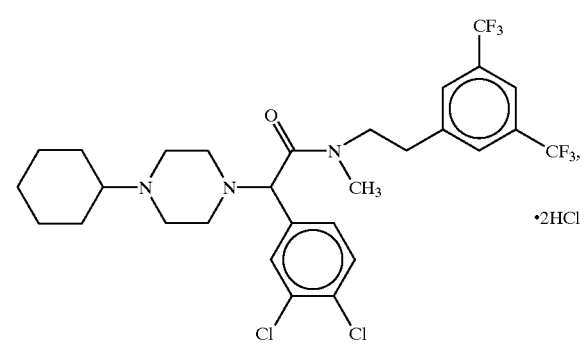
•2HCl
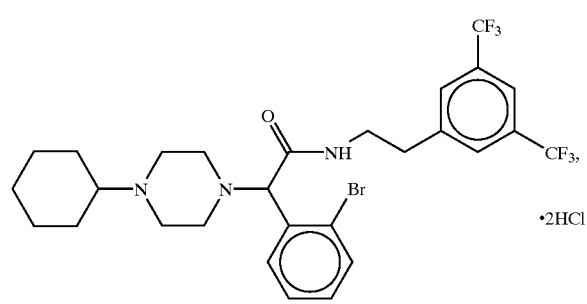
•2HCl
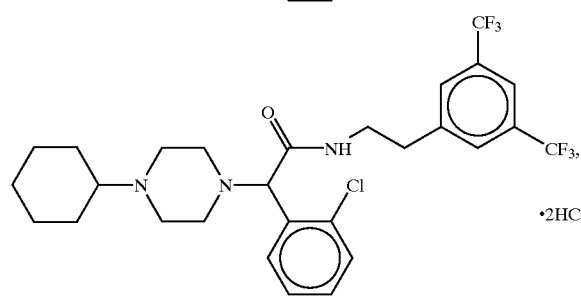
•2HCl
-continued
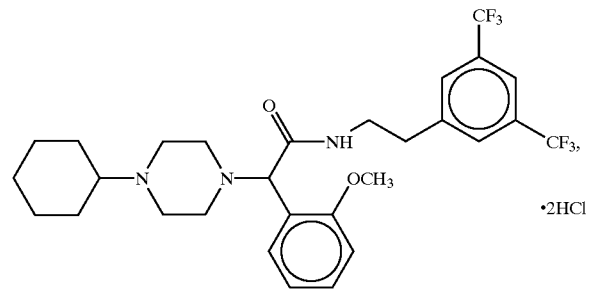
•2HCl
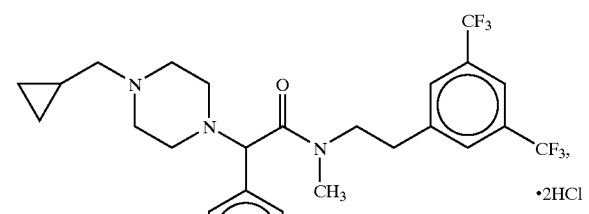
•2HCl
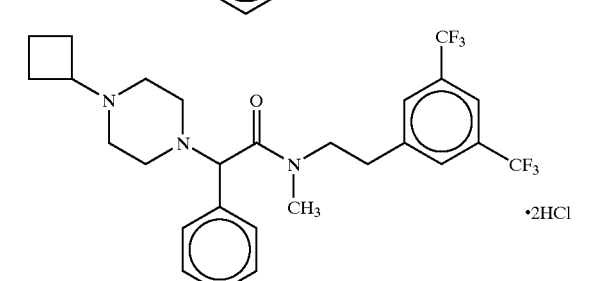
•2HCl
and
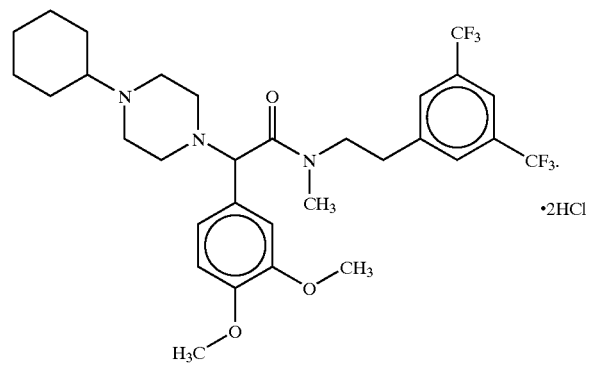
•2HCl
18. The method of claim 17, wherein said compound is
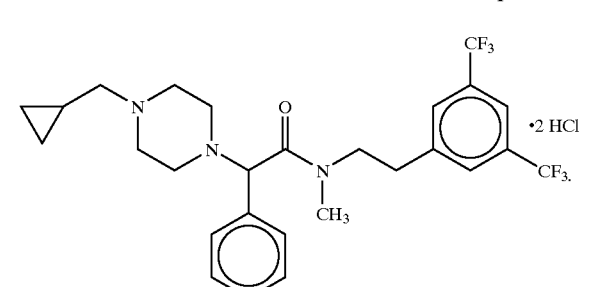
•2 HCl 19. The method of claim 5 wherein Ar is phenyl having 0, 1, 2 or 3 substitucnts.

20. The method of claim 19, wherein Ar is phenyl having at least one hydroxyl substituent.

21. The method of claim 19, wherein said compound is selected from the group consisting of

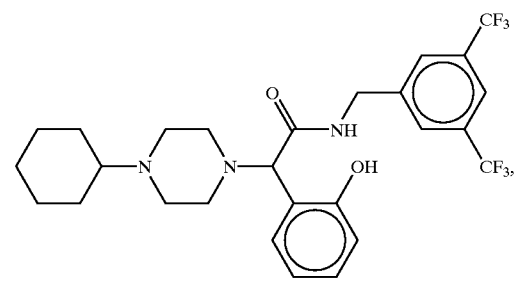

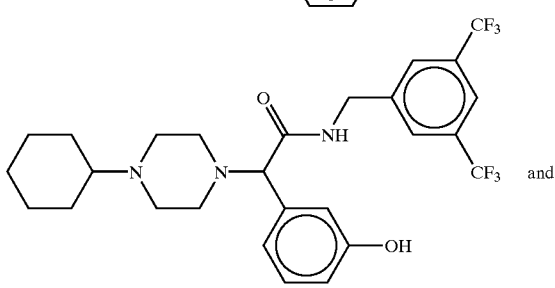

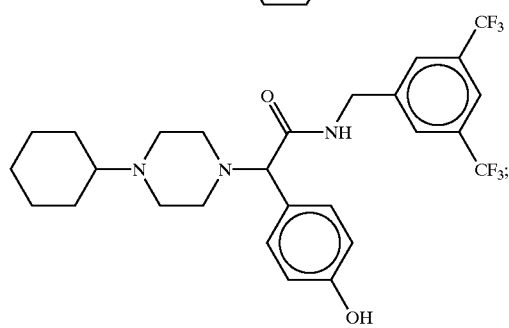

or a pharmaceutically acceptable salt thereof.

22. The method of claim 21, wherein said pharmaceutically acceptable salt is an HCl salt.

23. The method of claim 5, wherein Ar is phenyl having a substituent selected from the group consisting of —OCH$_2$O— and —O(CH$_2$)$_2$O—.

24. The method of claim 23, wherein said compound is

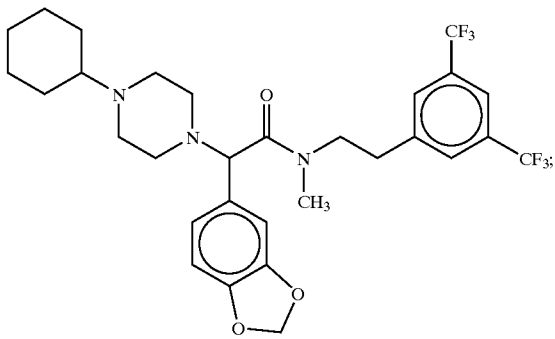

or a pharmaceutically acceptable salt thereof.

25. The method of claim 24, wherein said compound is

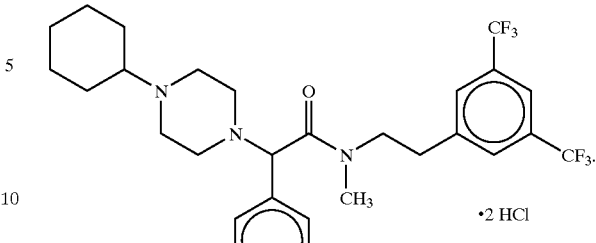

26. The method of claim 25, wherein $R^3$ is hydrogen or methyl.

27. The method of claim 5, wherein $R^4$ is phenyl($C_{1-4}$) alkyl, wherein the phenyl is unsubstituted or mono- to tri-substituted.

28. The method of claim 27, wherein $R^4$ is phenyl($C_{1-4}$) alkyl, wherein the phenyl is substituted by one, two, or three trifluoromethyl groups.

29. The method of claim 28, wherein $R^4$ is

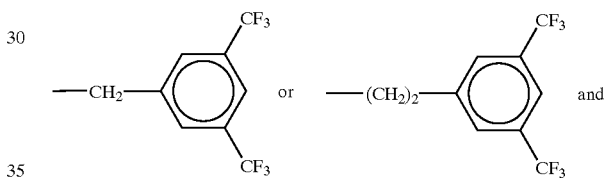

$R^5$ is hydrogen or methyl.

30. The method of claim 5, wherein $R^5$ is hydrogen or ($C_{1-4}$)alkyl.

31. The method of claim 1, wherein X is $CR^7R^8$, wherein $R^7$ and $R^8$ have one of the following meanings:

(a) $R^7$ and $R^8$ are each hydrogen when $R^3$ is unsubstituted or substituted phenyl;

(b) $R^7$ is phenyl, phenyl substituted by 1 to 3 substituents, wherein the substituents are independently selected from the group consisting of halogen, ($C_{1-4}$)alkyl, O—($C_{1-4}$)alkyl, $CF_3$ and $OCF_3$, piperidinyl, 1-methylpiperidinyl,

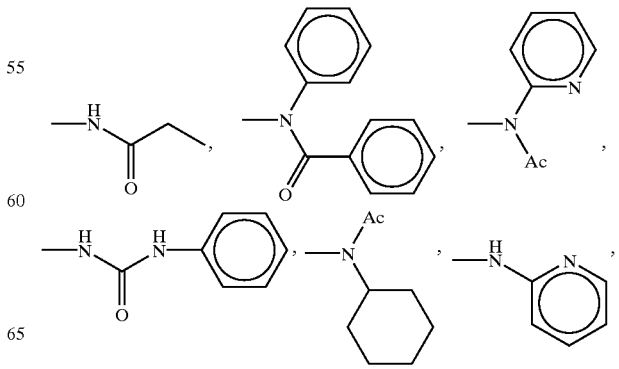

-continued

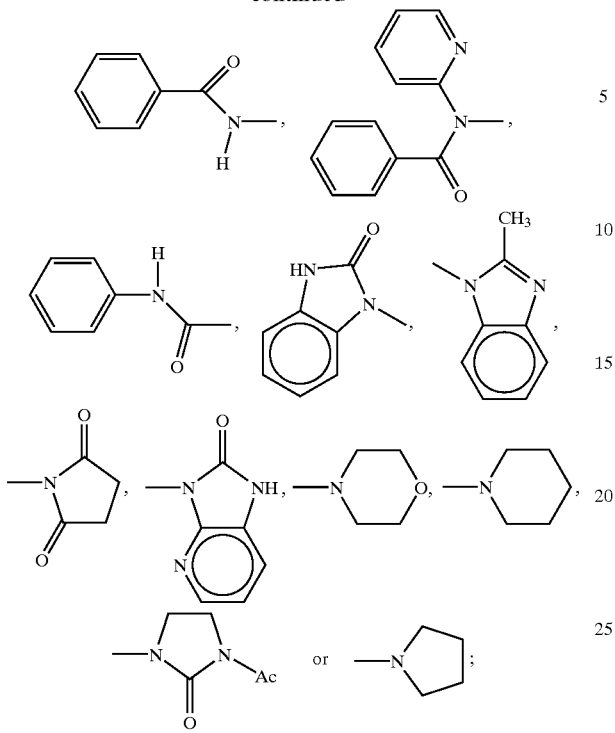

when R[8] is hydrogen, —CONH$_2$, —NHC(O)CH$_3$, —N(CH$_3$)C(O)CH$_3$, CN, —C(O)NH(C$_{1-3}$)alkyl, or —C(O)N((C$_{1-3}$)alkyl)$_2$; or
(c) R[7] and R[8] together form the group

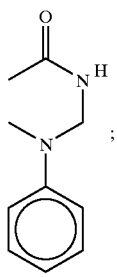

R[3] is hydrogen, (C$_{1-4}$)alkyl, unsubstituted phenyl or mono- to tri-substituted phenyl, wherein the substituents are independently selected from the group consisting of halogen, (C$_{1-4}$)alkyl, O—(C$_{1-4}$)alkyl, CF$_3$, OCF$_3$ and NR$^9$R$^{10}$, wherein R$^9$ and R$^{10}$ are independently selected from the group consisting of hydrogen, methyl and acetyl;

R[4] is phenyl (C$_{1-4}$)alkyl or naphthyl (C$_{1-4}$)alkyl, wherein phenyl is optionally substituted by 1 to 3 substituents, independently selected from the group consisting of halogen, (C$_{1-4}$)alkyl, O—(C$_{1-4}$)alkyl, CF$_3$, OCF$_3$ and NR$^9$R$^{10}$, wherein R$^9$ and R$^{10}$ are independently selected from the group consisting of hydrogen, methyl and acetyl; and R[5] is hydrogen, (C$_{1-4}$)alkyl, (C$_{3-6}$)cycloalkyl, CH$_2$COOH, —CH$_2$C(O)NH$_2$, hydroxy or phenyl (C$_{1-4}$)alkyl.

32. The method of claim 31, wherein R$^3$ is unsubstituted or substituted phenyl and R$^7$ and R$^8$ are each hydrogen.

33. The method of claim 32, wherein said compound is selected from the group consisting of

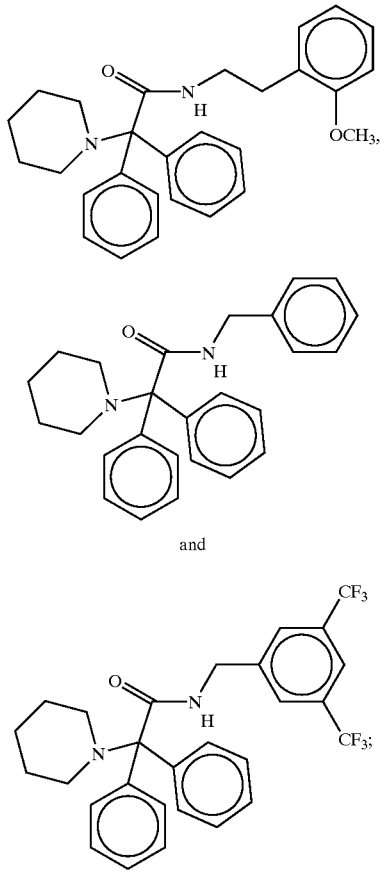

or a pharmaceutically acceptable salt thereof.

34. The method of claim 33, wherein said pharmaceutically acceptable salt is an HCL salt.

35. The method of claim 31, wherein R$^7$ and R$^8$ together form the group

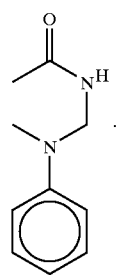

36. The method of claim 35, wherein said compound is selected from the group consisting of

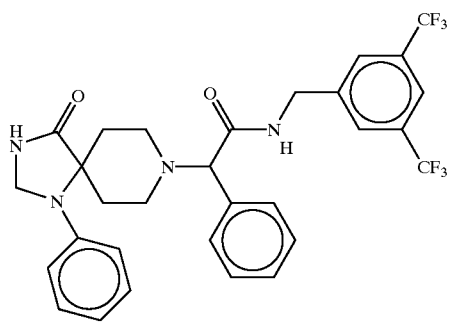
and
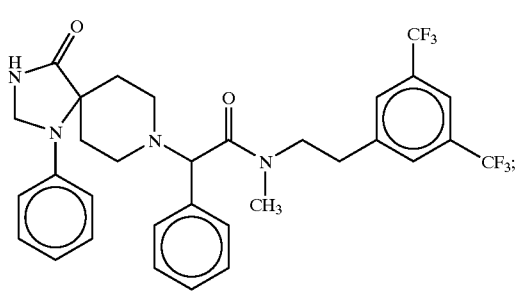
or a pharmaceutically acceptable salt thereof.
37. The method of claim 36, wherein said pharmaceutically acceptable salt is an HCl salt.
38. The method of claim 37, wherein said compound is
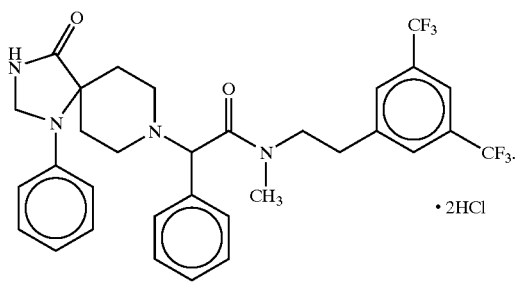
39. The method of claim 31, wherein $R^7$ is other than hydrogen and $R^8$ is hydrogen.
40. The method of claim 39, wherein said compound is selected from the group consisting of
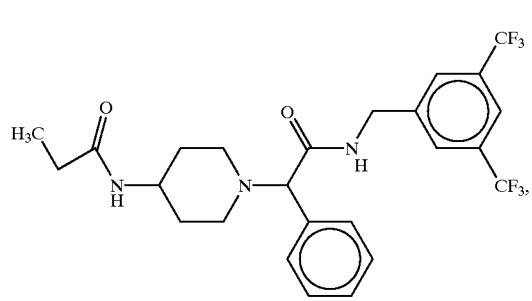
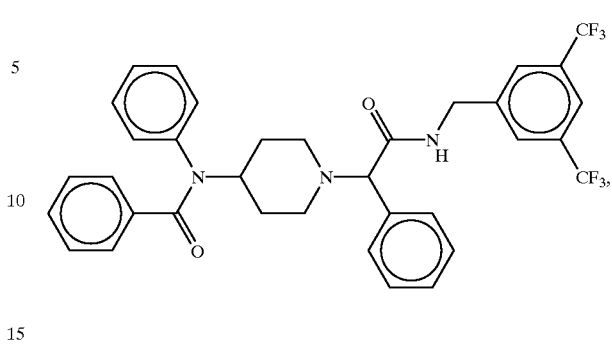
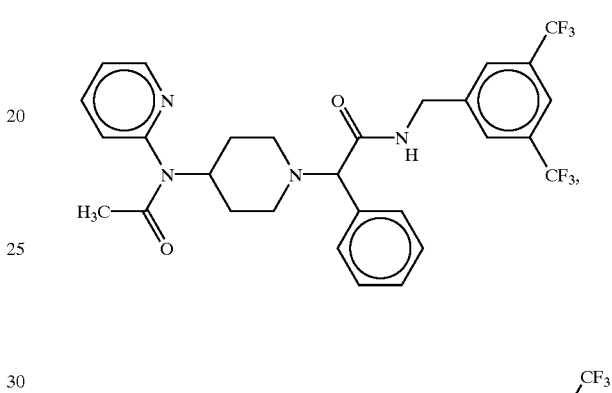
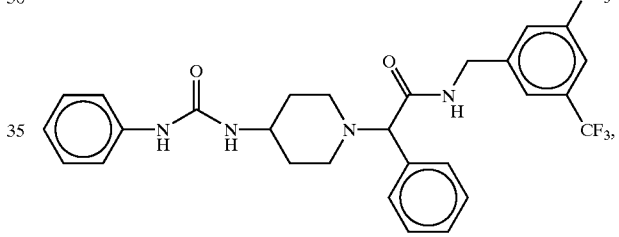
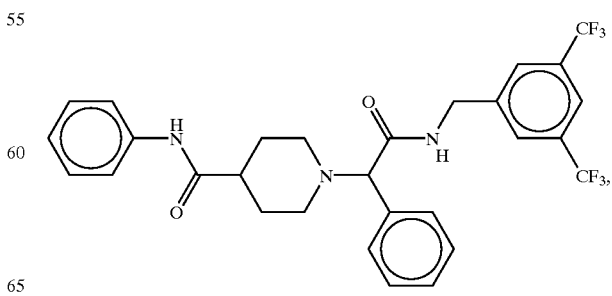

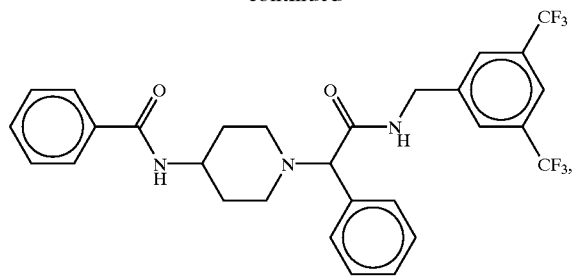
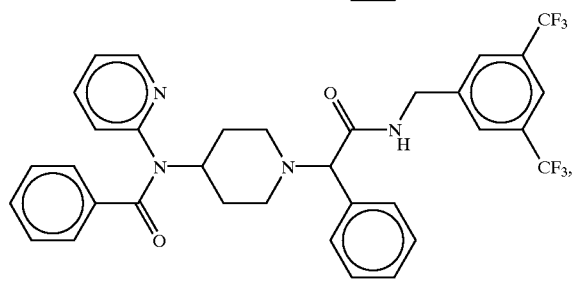
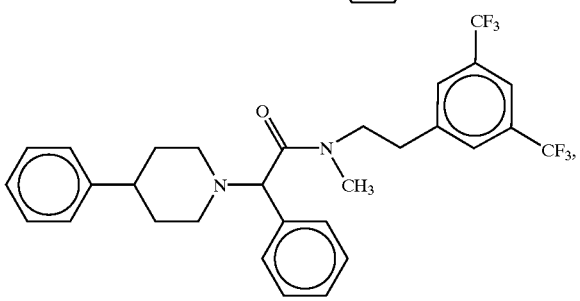
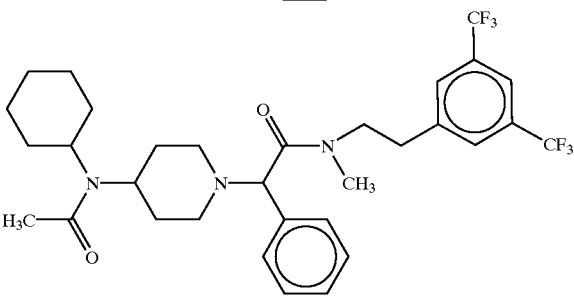
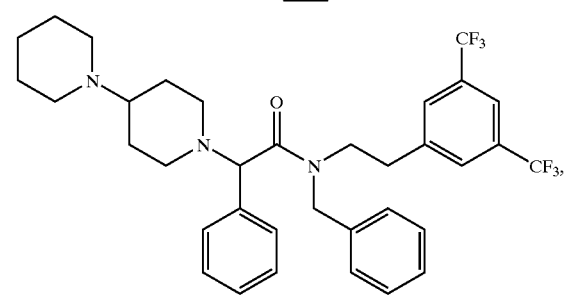
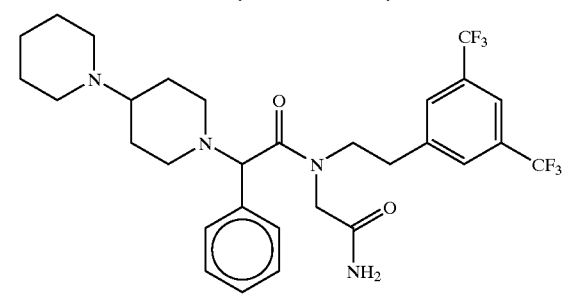
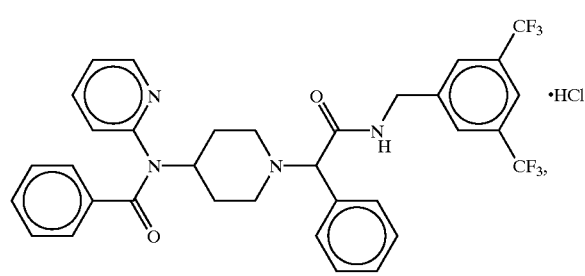
or a pharmaceutically acceptable salt thereof.
41. The method of claim 40, wherein said pharmaceutically acceptable salt is an HCl salt.
42. The method of claim 41, wherein said compound is selected from the group consisting of
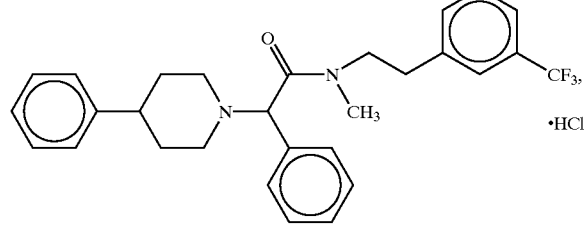
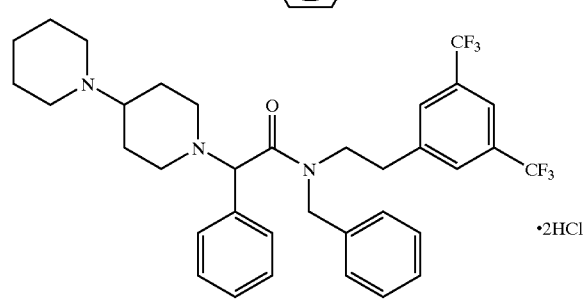
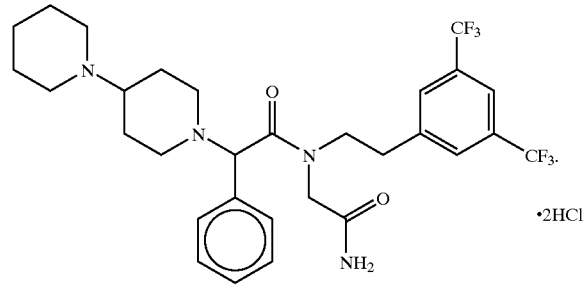

43. The method of claim 31, wherein R⁸ is selected from the group consisting of —NHC(O)CH₃ and —N(CH₃)C(O)CH₃.

44. The method of claim 43, wherein said compound is selected from the group consisting of

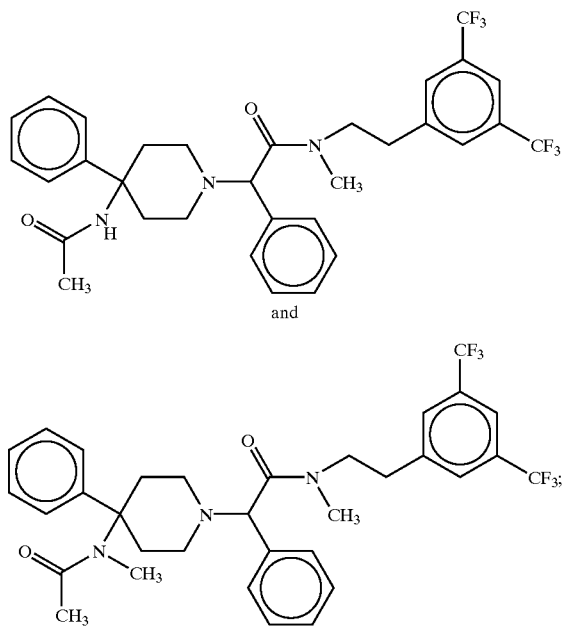

or a pharmaceutically acceptable salt thereof.

45. The method of claim 44, wherein said pharmaceutically acceptable salt is an HCl salt.

46. The method of claim 31, wherein R⁸ is selected from the group consisting of CN, —C(O)NH₂, —C(O)NH(C₁₋₃)alkyl and —C(O)N((C₁₋₃)alkyl)₂.

47. The method of claim 46, wherein said compound is selected from the group consisting of

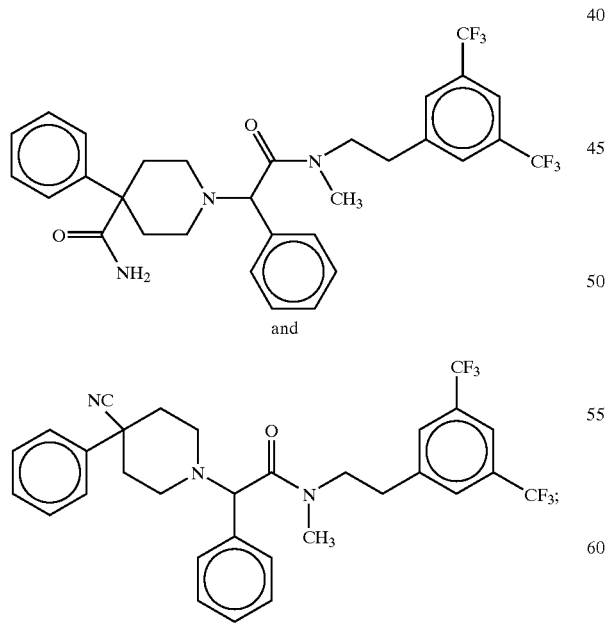

or a pharmaceutically acceptable salt thereof.

48. The method of claim 47, selected from the group consisting of

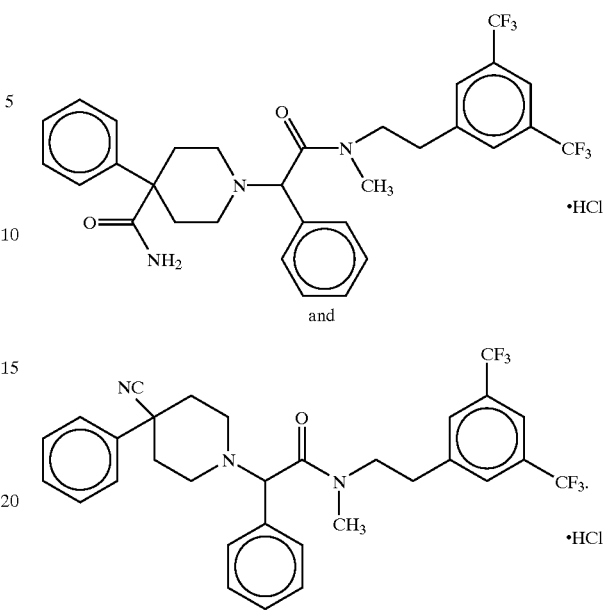

49. The method of claim 31, wherein R³ is hydrogen.

50. The method of claim 31, wherein R³ is unsubstituted phenyl.

51. The method of claim 31, wherein R³ is mono- to tri-substituted phenyl.

52. The compound of claim 31, wherein R⁴ is phenyl (C₁₋₃) alkyl, wherein said phenyl is optionally substituted by 1 or 2 substituents, independently selected from the group consisting of halogen, methyl, methoxy, CF₃ and OCF₃; and R⁵ is selected from the group consisting of hydrogen, (C₁₋₃) alkyl, CH₂COOH, —CH₂C(O)NH₂ and phenethyl.

53. The method of claim 52, wherein R⁴ is

R⁵ is hydrogen or methyl.

54. The method of claim 31, wherein R⁷ is

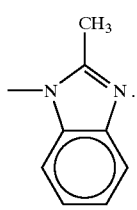

55. The method of claim 54, wherein said compound is

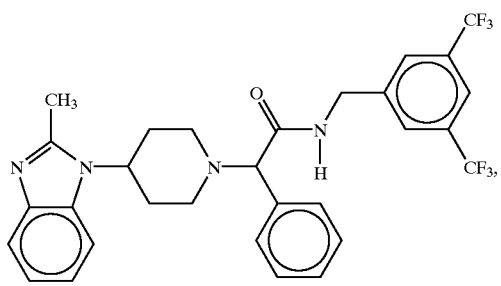

or a pharmaceutically acceptable salt thereof.

56. The method of claim 55, wherein said pharmaceutically acceptable salt is an HCl salt.

57. The method of claim 31, wherein $R^7$ is

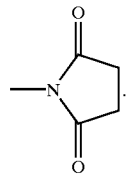

58. The method of claim 57, wherein said compound is

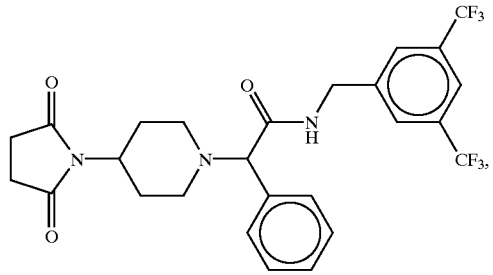

or a pharmaceutically acceptable salt thereof.

59. The method of claim 58, wherein said compound is

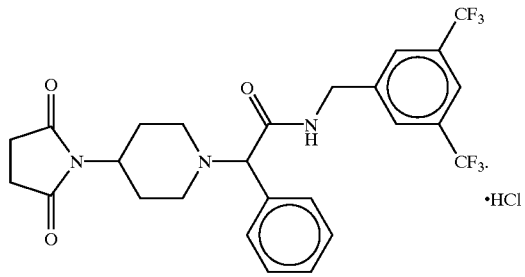

60. The method of claim 31, wherein $R^7$ is

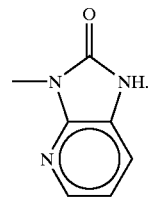

61. The method of claim 60, wherein said compound is

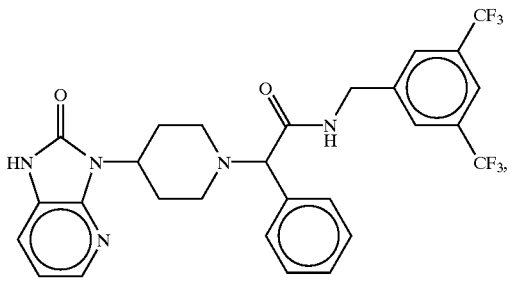

or a pharmaceutically acceptable salt thereof.

62. The method of claim 61, wherein said pharmaceutically acceptable salt is an HCl salt.

63. The method of claim 31, wherein $R^7$ is 4-morpholino.

64. The method of claim 63, wherein said compound is

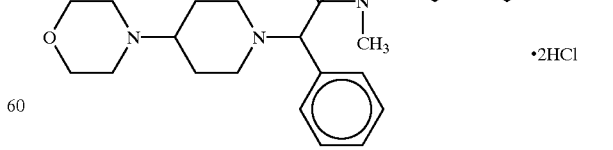

or a pharmaceutically acceptable salt thereof.

65. The method of claim 64, wherein said compound is

66. The method of claim 31, wherein $R^7$ is 1-piperidinyl.

67. The method of claim 66, wherein said compound is selected from the group consisting of:

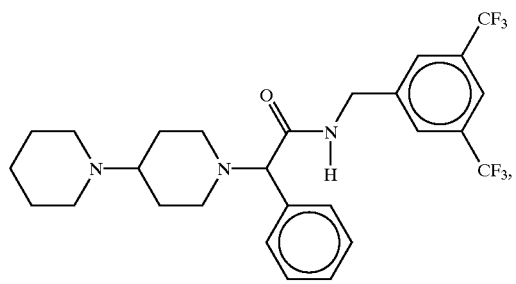
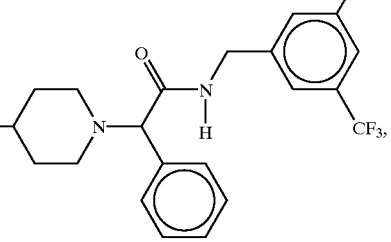
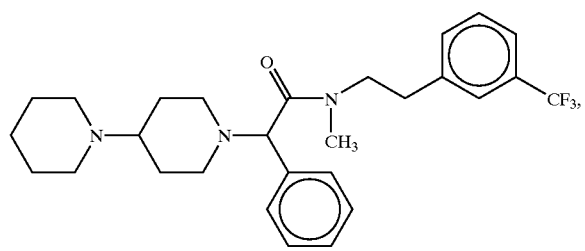
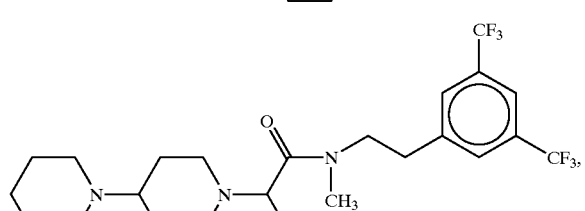
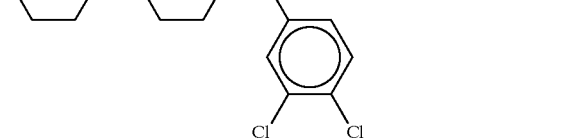
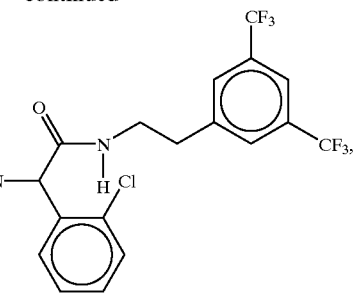
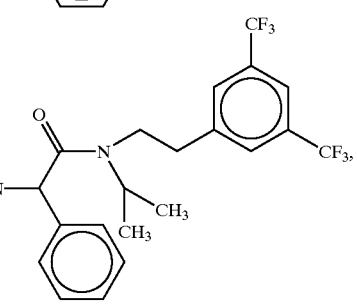
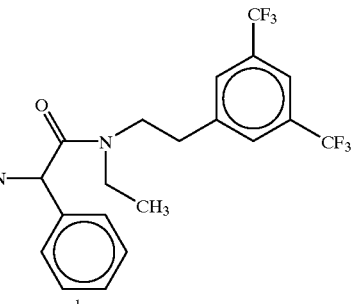
and
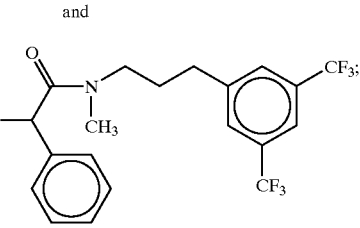
or a pharmaceutically acceptable salt thereof.
68. The method of claim 67, wherein said pharmaceutically acceptable salt is an HCl salt.
69. The method of claim 68, wherein said compound is

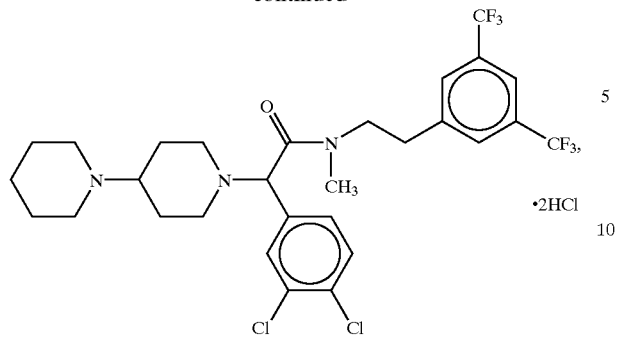

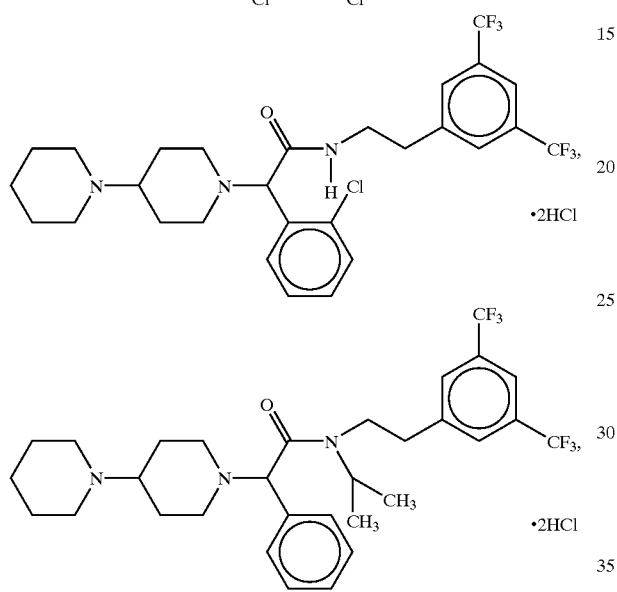

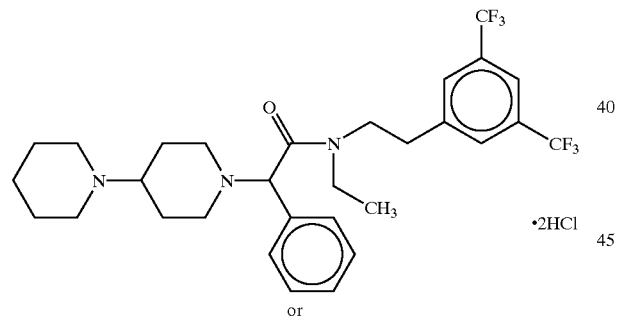

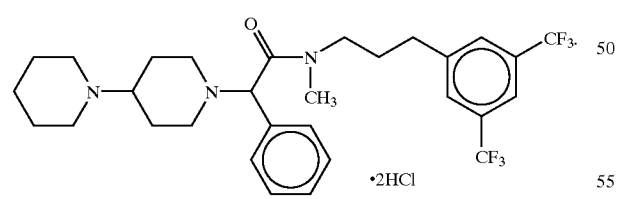

70. The method of claim 31, wherein R⁷ is

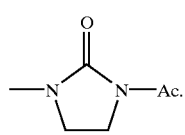

71. The method of claim 70, wherein said compound is

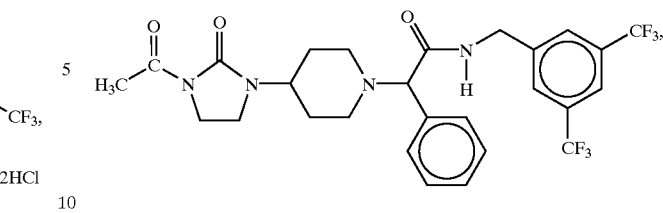

or a pharmaceutically acceptable salt thereof.

72. The method of claim 71, wherein said pharmaceutically acceptable salt is an HCl salt.

73. The method of claim 31, wherein R⁷ is 1-pyrrolidinyl.

74. The method of claim 73, wherein said compound is

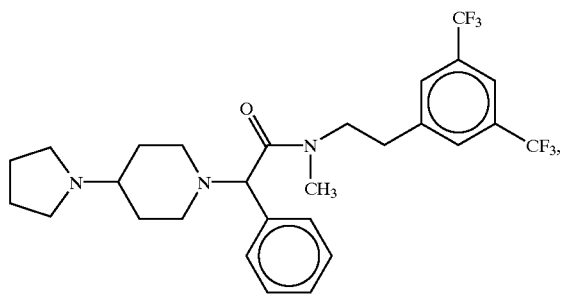

or a pharmaceutically acceptable salt thereof.

75. The method of claim 74, wherein said compound is

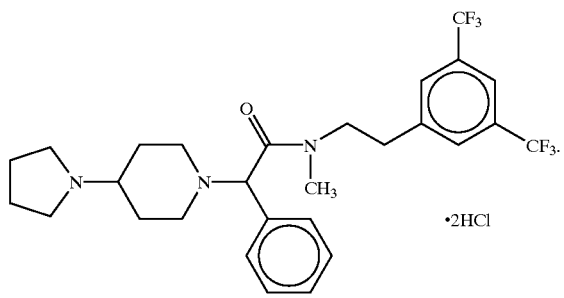

76. The method of claim 31, wherein Ar is phenyl having 0, 1, 2 or 3 substituents.

77. The method of claim 31, wherein $R^3$ is hydrogen or methyl.

78. The method of claim 31, wherein $R^3$ is unsubstituted phenyl.

79. The method of claim 31, wherein $R^3$ is mono- to tri-substituted phenyl.

80. The method of claim 31, wherein $R^4$ is phenyl($C_{1-3}$) alkyl, wherein said phenyl is optionally substituted by 1 or 2 substituents independently selected from the group consisting of halogen, methyl, methoxy, $CF_3$ and $OCF_3$; and $R^5$ is selected from the group consisting of hydrogen ($C_{1-3}$) alkyl, $CH_2COOH$, —$CH_2C(O)NH_2$ and phenethyl.

81. The method of claim 80, wherein $R^4$ is

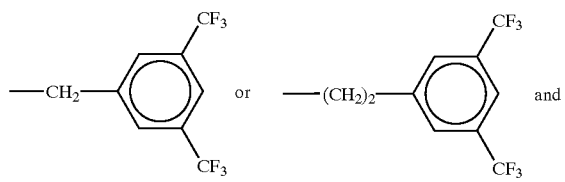

$R^5$ is hydrogen or methyl.

82. The method of claim 31, wherein $R^5$ is hydrogen or $(C_{1-4})$alkyl.

83. The method of claim 31, wherein $R^8$ is hydrogen.

84. The method of claim 31, wherein $R^8$ is selected from the group consisting of —NHC(O)CH$_3$ and —N(CH$_3$)C(O)CH$_3$.

85. The method of claim 31, wherein $R^8$ is selected from the group consisting of CN, —C(O)NH$_2$, —C(O)NH(C$_{1-3}$)alkyl and —C(O)N((C$_{1-3}$)alkyl)$_2$.

* * * * *